United States Patent [19]

Hiruta et al.

[11] Patent Number: 5,111,539

[45] Date of Patent: May 12, 1992

[54] TOILET DEVICE WITH SYSTEM FOR INSPECTING HEALTH CONDITIONS

[75] Inventors: Yoshiki Hiruta; Naoki Tsukamura; Yoshinobu Uchimura; Toshifumi Shigematsu; Hironori Yamasaki; Toshio Yamaguchi, all of Fukuoka, Japan

[73] Assignee: Toto Ltd., Fukuoka, Japan

[21] Appl. No.: 573,645

[22] Filed: Aug. 27, 1990

[30] Foreign Application Priority Data

| Aug. 25, 1989 | [JP] | Japan | 1-99193 |
| Aug. 25, 1989 | [JP] | Japan | 1-99200 |
| Aug. 25, 1989 | [JP] | Japan | 1-99203 |
| Aug. 25, 1989 | [JP] | Japan | 1-99208 |
| Aug. 25, 1989 | [JP] | Japan | 1-219211 |
| Aug. 25, 1989 | [JP] | Japan | 1-219214 |
| Aug. 25, 1989 | [JP] | Japan | 1-219217 |
| Aug. 25, 1989 | [JP] | Japan | 1-219218 |

[51] Int. Cl.$^5$ .................... E03B 11/02; G01N 33/493
[52] U.S. Cl. ........................... 4/661; 4/301; 4/420; 4/314; 128/736; 128/760
[58] Field of Search ............ 4/314, 661, 420, 443, 4/318, 301, 444; 128/677, 760, 771, 632, 736; 73/864.81–864.85

[56] References Cited

U.S. PATENT DOCUMENTS

| 4,466,445 | 8/1984 | Abrams | 128/736 |
| 4,524,777 | 6/1985 | Kisioka et al. | 128/677 |
| 4,636,474 | 1/1987 | Ogura et al. | 4/314 |
| 4,901,736 | 2/1990 | Huang | 128/760 |
| 4,961,431 | 10/1990 | Ikenaga et al. | |
| 4,962,550 | 10/1990 | Ikenaga | 4/314 X |

FOREIGN PATENT DOCUMENTS

| 292311 | 11/1988 | European Pat. Off. | 4/314 |
| 308080 | 3/1989 | European Pat. Off. | 4/314 |
| 57-59168 | 4/1982 | Japan . | |
| 60-117157 | 6/1985 | Japan . | |
| 60-233551 | 11/1985 | Japan . | |
| 63-21555 | 1/1988 | Japan . | |
| 63-184057 | 7/1988 | Japan . | |

Primary Examiner—Charles E. Phillips
Attorney, Agent, or Firm—Irving M. Weiner; Joseph P. Carrier; Pamela S. Burt

[57] ABSTRACT

A toilet device with a system for inspecting the health condition of the toilet user includes a toilet having a bowl surface with a urine reservoir for holding a urine sample, a box having at least a water tank disposed rearwardly and upwardly of the toilet, the box having an outlet opening in a bottom thereof, a slider for holding a urine test paper piece, the slider being movable from within the box toward the urine reservoir to immerse the urine test paper piece in the urine sample in the urine reservoir, a urine analyzing device disposed in the box, for analyzing constituents of the urine sample attached to the urine test paper piece, a lifting and lowering mechanism for reciprocally lifting and lowering the slider through the outlet opening along a substantially vertical inclined path between the urine analyzing device and the urine reservoir, and a display panel for controlling the lifting and lowering mechanism and the urine analyzing device and for displaying results of a urine analysis effected by the urine analyzing device.

35 Claims, 25 Drawing Sheets

FIG. 5
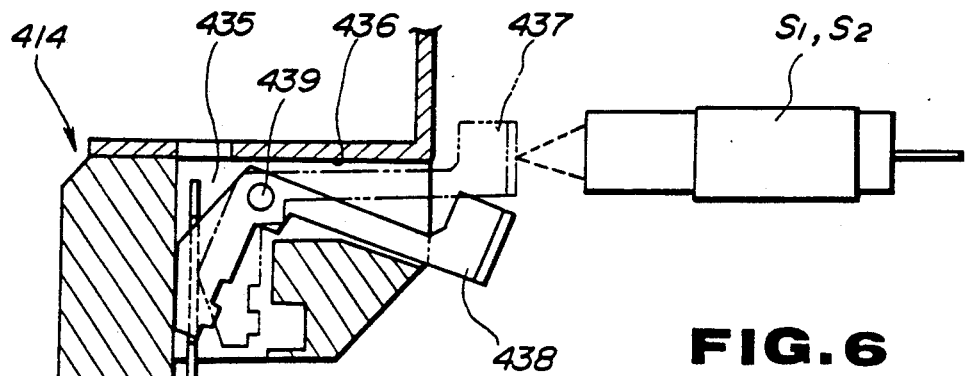
FIG. 6
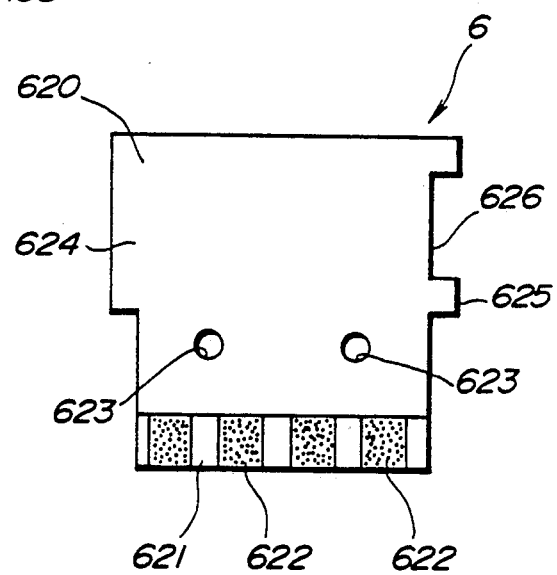
FIG. 7
|  | SENSOR S1 | SENSOR S2 | JUDGMENT |
|---|---|---|---|
| PRIOR TO INSERTION | OFF | OFF | NOT INSERTED |
| TYPE 1 | OFF | ON | INSERTED PROPERLY |
| TYPE 2 | ON | OFF | INSERTED ERRONEOUSLY |

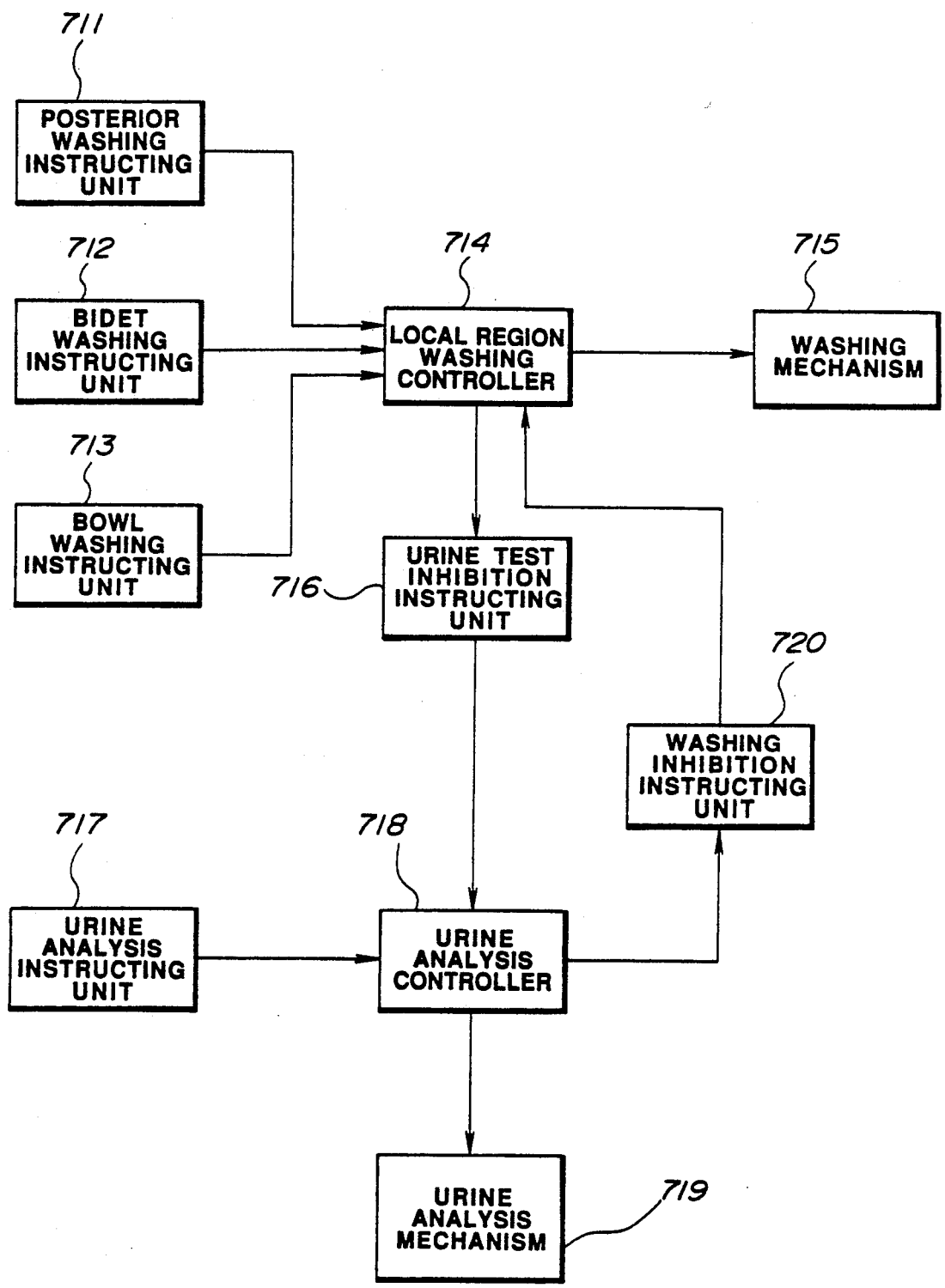

TOILET DEVICE WITH SYSTEM FOR INSPECTING HEALTH CONDITIONS

BACKGROUND OF THE INVENTION

1. Field of the Invention

The present invention relates to a toilet device having a system for inspecting health conditions of toilet users through a urine analysis.

2. Description of the Relevant Art

Recently, there have been known various toilet devices with a urine analyzer coupled to a toilet for analyzing the urine of a user of the toilet. According to the toilet device disclosed in Japanese Laid-Open Patent Publication No. 57(1982)-59168, a urine sample is extracted when the user of the toilet urinates, and a piece of urine test paper is immersed in the urine sample manually by the user and thereafter set in a urine analyzer. Since the test paper with the urine sample attached is manually set in the urine analyzer, the disclosed toilet device has a sanitary problem. Japanese Laid-Open Patent Publications Nos. 60(1985)-117157 and 63(1988)-21555 disclose toilet devices which have conduits opening at the inner surface of toilet bowls for transferring a urine sample from the bowls to urine analyzing mechanisms. Although these disclosed systems are free of any sanitary problem, since the conduits in the toilets are relatively long, the toilets are complex in structure, and the conduits tend to get clogged and cannot be easily cleaned.

The toilet devices are required to have a display panel for displaying, as health data, the results of the analysis of certain constituents of the sampled urine. One such display panel is disclosed in Japanese Laid-Open Patent Publication No. 63(1988)-184057. The disclosed display panel displays the results as quantitative values to the accuracy of the order of 1, and has marks indicating positive, false positive, and negative, on one side of the area for displaying the results.

The health data display panel is essentially used to give a simple indication of the proportions of glucose, albumin, and other constituents of urine while the user is urinating. Therefore, the accuracy of the order of 1 may not be useful to the user. The marks indicating positive, false positive, and negative are not specific enough for the user to understand his health conditions quickly.

SUMMARY OF THE INVENTION

In view of the aforesaid drawbacks of the conventional toilet devices with health condition test systems, it is an object of the present invention to provide a toilet device having a system for inspecting health conditions of toilet users, the system including an inspecting mechanism such as a urine analyzing mechanism capable of smoothly inspecting health conditions through a urine analysis, for example, in a sanitary fashion, the inspecting mechanism being accommodated compactly in a toilet and toilet-related components without having to largely modify the normal toilet structure.

According to the present invention, there is provided a toilet device with a system for inspecting the health condition of the toilet user, which toilet device includes a toilet having a bowl surface with a urine reservoir for holding a urine sample, a box having at least a water tank disposed rearwardly and upwardly of the toilet, the box having an outlet opening in a bottom thereof, a slider for holding a urine test paper piece, the slider being movable from within the box toward the urine reservoir to immerse the urine test paper piece in the urine sample in the urine reservoir, a urine analyzing device disposed in the box, for analyzing constituents of the urine sample attached to the urine test paper piece, and a lifting and lowering mechanism for reciprocally lifting and lowering the slider through the outlet opening along a substantially vertical inclined path between the urine analyzing device and the urine reservoir. Preferably, the toilet device also has a display panel mounted on a side of the bathroom in which the toilet device is installed, the display pane controlling the lifting and lowering mechanism and the urine analyzing device and displaying results of a urine analysis effected by the urine analyzing device.

The above and further objects, details and advantages of the present invention will become apparent from the following detailed description of preferred embodiments thereof, when read in conjunction with the accompanying drawings.

BRIEF DESCRIPTION OF THE DRAWINGS

FIG. 5 is a cross-sectional view of a holder for holding a piece of urine test paper, in the lifting/lowering mechanism shown in FIG. 4;

FIG. 6 is a plan view of a piece of urine test paper held by the holder shown in FIG. 5;

FIG. 7 is a table showing the relationship between sensor signals and inserted modes of the piece of urine test paper shown in FIG. 6 when the latter is inserted into the holder shown in FIG. 5;

FIG. 29 is a block diagram of a mutual operation deterring mechanism which can be employed in the toilet device according to the present invention;

DETAILED DESCRIPTION OF THE PREFERRED EMBODIMENTS

Figure 1:
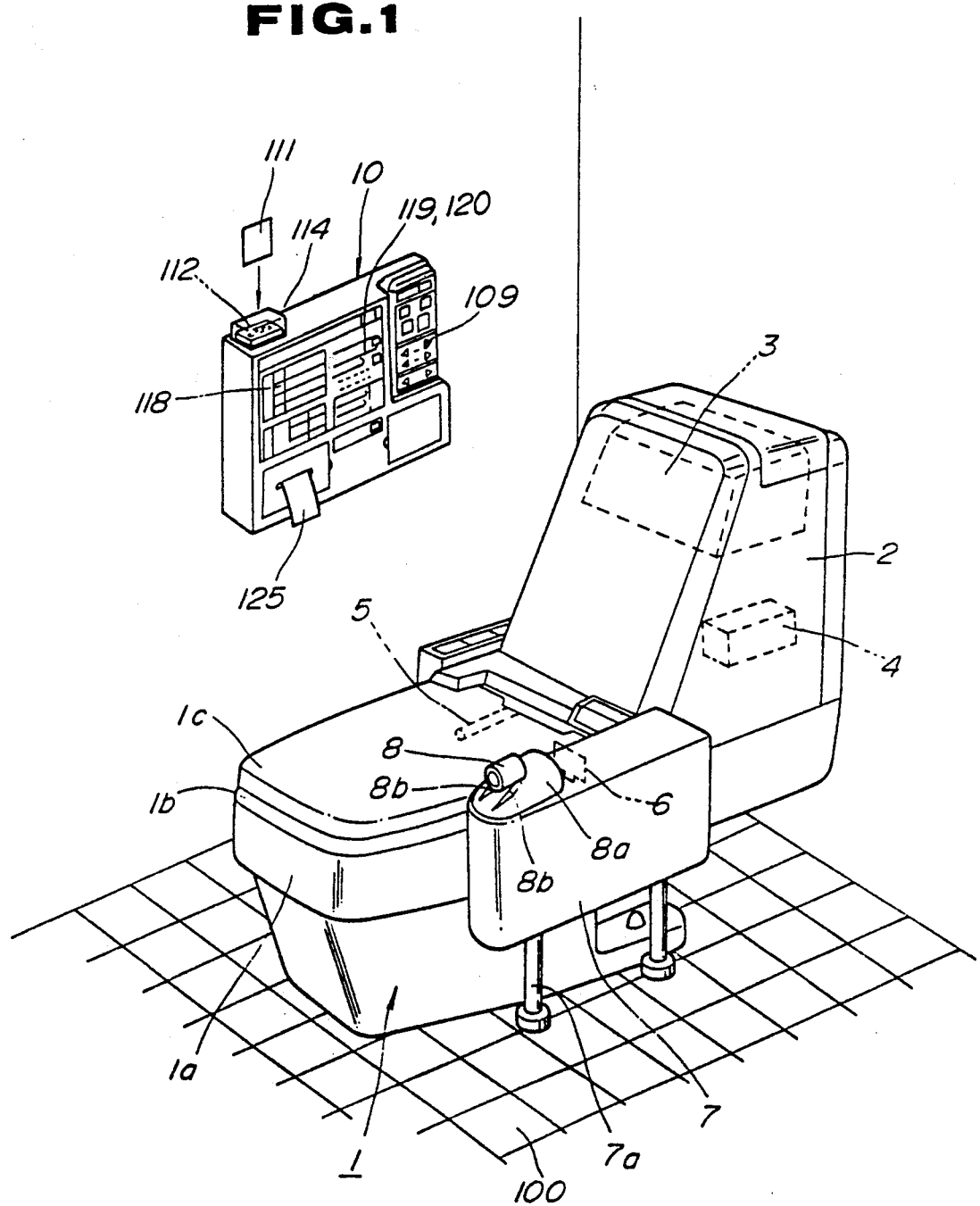
FIG. 1 is a schematic perspective view of a bathroom in which a toilet device according to the present invention is installed.

FIG. 1 shows in perspective a bathroom in which a toilet device with a system for inspecting health conditions according to the present invention is installed.

As shown in FIG. 1, a toilet 1 is mounted on a floor 100, and has a seat 1b on a rim 1a and a lid 1c disposed over the seat 1b. A box 2, which is disposed rearwardly and upwardly of the toilet 1, houses a water tank 3 and a urine analyzing device 4 therein. The box 2 also houses a local region washing device which includes a local region washer 5 that ca be extended into and retracted from a bowl (described later) of the toilet 1. A blood pressure measuring control box 7 is disposed on one side (righthand side in the illustrated embodiment) of the toilet 1. The blood pressure measuring control box 7 has a blood pressure measuring cuff 8 mounted on a front upper surface thereof and accommodates a source of air under pressure and a cylinder unit. A display panel 10 is attached to a wall of the bathroom which is on the lefthand side of the toilet 1. The display panel 10 is in the form of a box, and is connected to the urine analyzing device 4, the blood pressure measuring control box 7, and various other actuating mechanisms through a communication cable (not shown in FIG. 1). The display panel 10 has at least a function to effect urine analyses, urine tests, and blood pressure measurements, and also a function to display the results of urine analyses and tests and the results of measurements. The control box 7 may be used to control the urine analyzing device and the local region washing device, other than blood pressure measurements.

Figure 2:
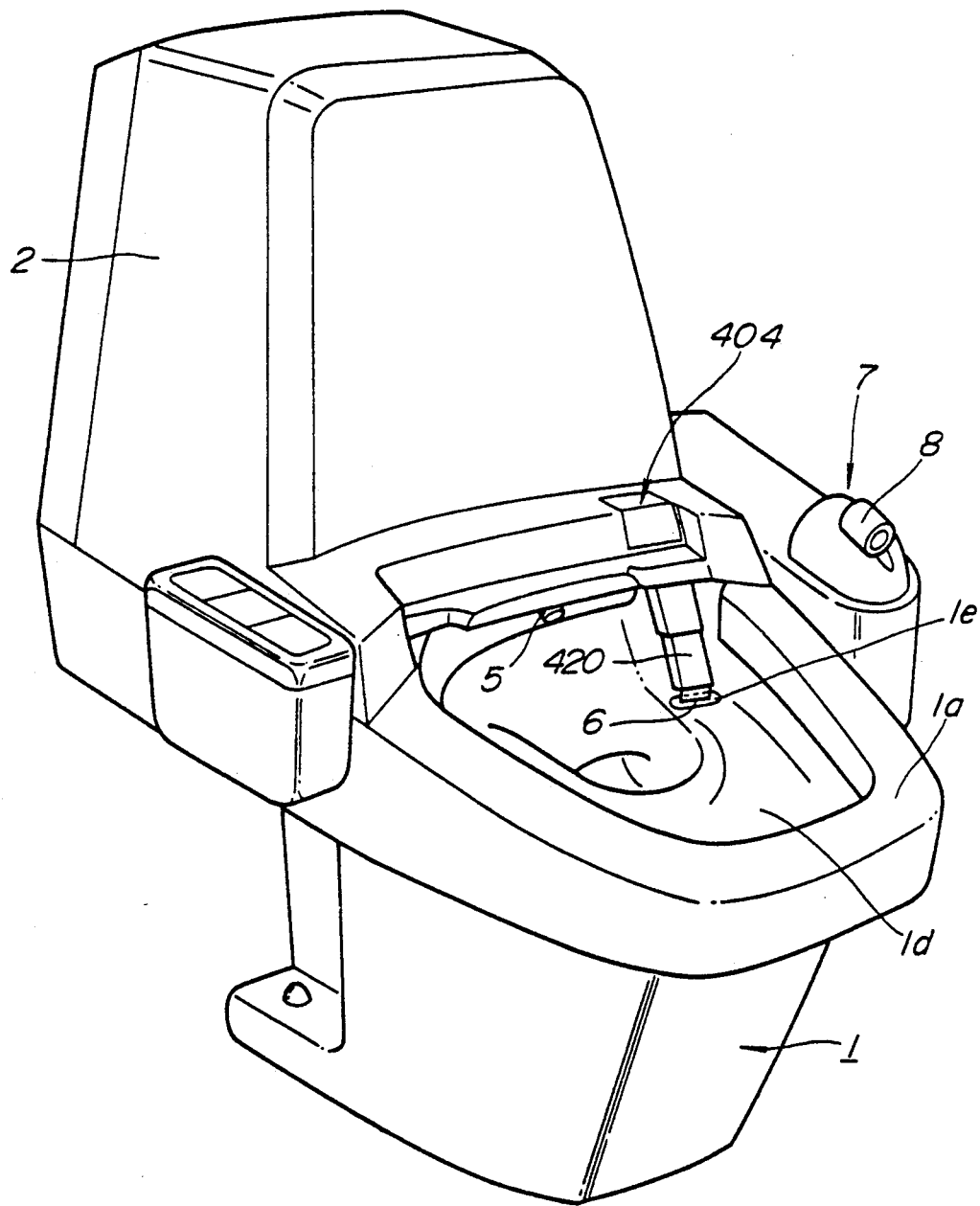
FIG. 2 is a perspective view of a toilet of the toilet device shown in FIG. 1.

FIG. 2 shows in perspective only, the toilet 1 and the box 2 as viewed in the opposite direction to the direction in which FIG. 1 is viewed. For the sake of brevity, the seat 1b and the lid 1c are omitted from illustration in FIG. 2. As shown in FIG. 2, the toilet 1 has a bowl surface 1d including a lowered urine reservoir 1e which is positioned in a righthand rear portion of the bowl surface 1d. The urine reservoir 1e is not limited to the illustrated position, but may be positioned anywhere else in view of the position of related components (described later) of the urine analyzing device 4. A piece 6 of urine test paper can be lowered into the urine reservoir 1e by a lifting/lowering mechanism 400 disposed in the box 2, so that the urine test paper piece 6 can be immersed in a urine sample in the urine reservoir 1e. After the urine test paper piece 6 has been immersed in the sampled urine for a given period of time, it is retracted upwardly by the lifting/lowering mechanism 400 into a position just in front of the urine analyzing device 4, by which the urine attached to the urine test paper piece 6 can optically be analyzed.

Figure 3:
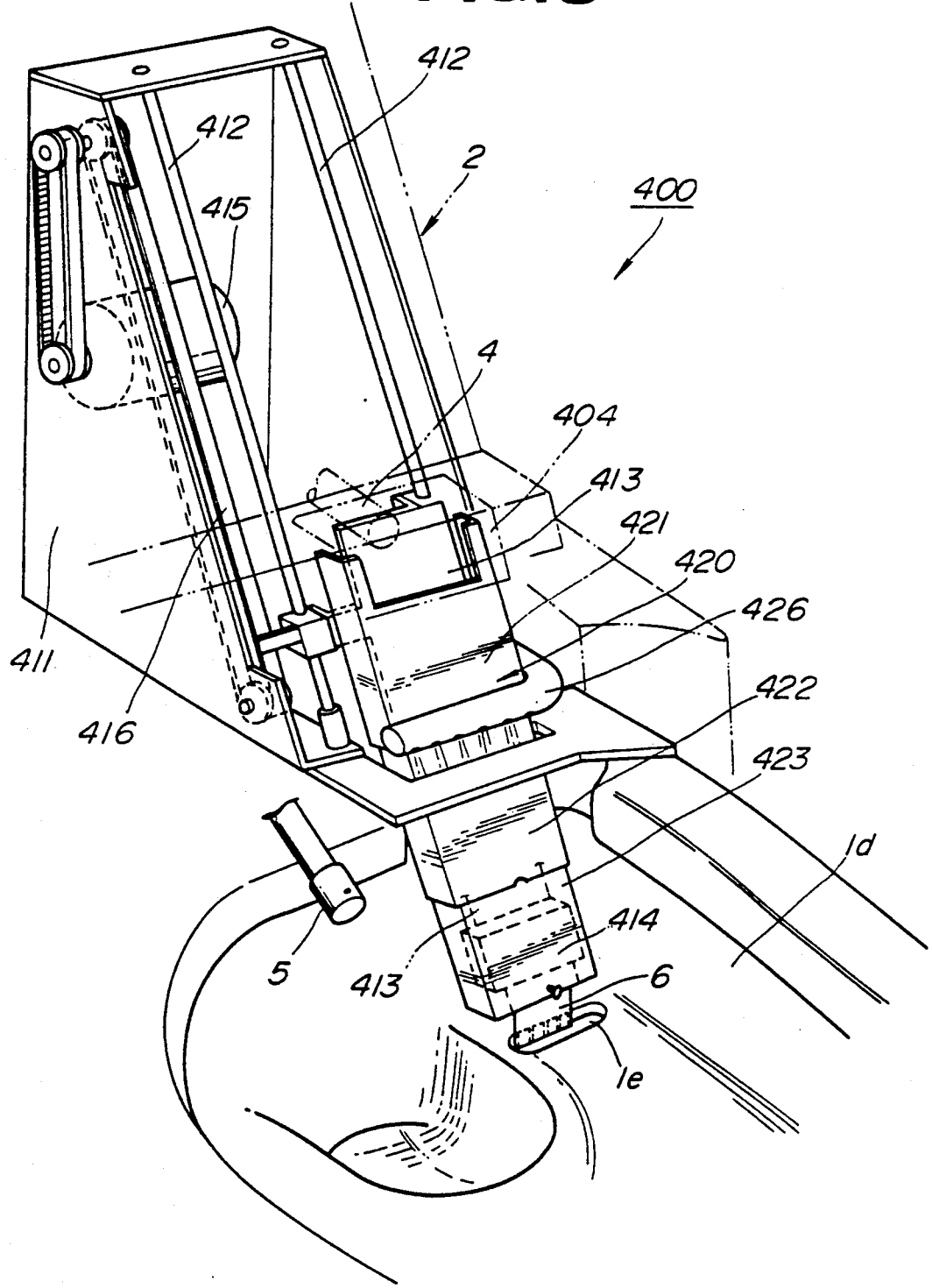
FIG. 3 is an enlarged fragmentary perspective view of a lifting/lowering mechanism in the toilet device shown in FIG. 1.
Figure 4:
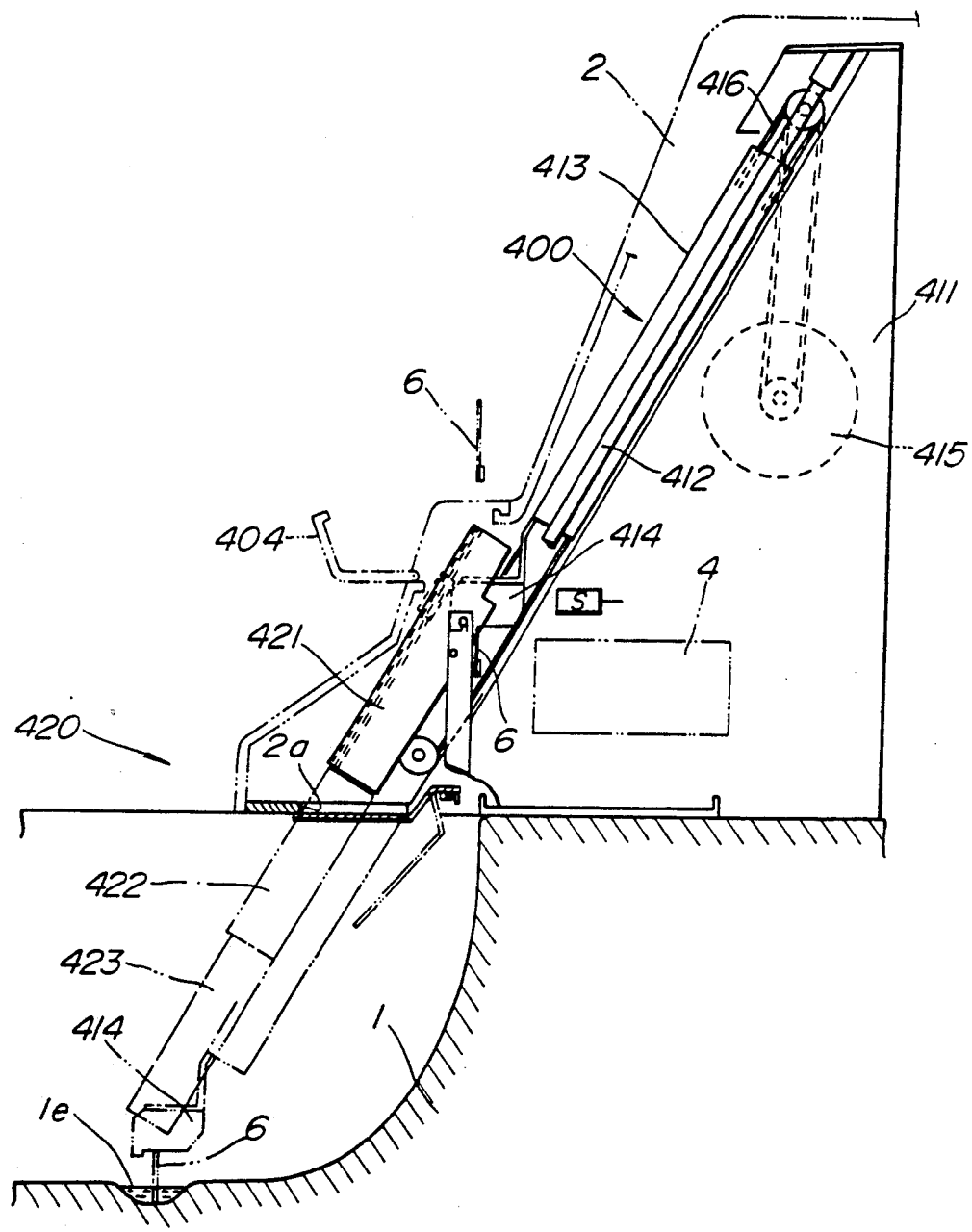
FIG. 4 is an enlarged fragmentary side elevational view of the lifting/lowering mechanism.

FIG. 3 shows in perspective the lifting/lowering mechanism 400 at an enlarged scale, and FIG. 4 shows in side elevation the lifting/lowering mechanism 400 at an enlarged scale.

The lifting/lowering mechanism 400 serves to move the urine test paper piece 6 reciprocally between the urine analyzing device 4 and the urine reservoir 1e. The lifting/lowering mechanism 400 and the urine analyzing device 4 are positioned in the righthand side of the box 2 so that they are spaced closely from the urine reservoir 1e which is disposed on the righthand side of the bowl surface 1d.

As shown in FIGS. 3 and 4, the lifting/lowering mechanism 400 includes a vertical frame 411 positioned in the box 2 and mounted on the toilet 1, and a pair of parallel guide rails 412 obliquely vertically supported on the frame 411. A slider 413 is slidably mounted on the guide rails 412 for linear movement on and along the guide rails 412. The urine test paper piece 6 is held by a holder 414 attached to the lower end of the slider 413. Preferably, the guide rails 412, which are inclined toward the urine reservoir 1e, extend between a position above the urine analyzing device 4 and an outlet opening 2a defined in the bottom of the box 2 for passage of the slider 413 therethrough.

The holder 214 can hold a new piece 6 of urine test paper vertically, which is inserted through a hole opened by a lid 404 hinged to a lower portion of a front wall of the box 2. After the urine sample attached to the urine test paper piece 6 has been analyzed, the urine test paper piece 6 is caused to drop into the urine reservoir 1e from the holder 414 by a remover mechanism (not shown) associated with the slider 413. As shown in FIG. 4, the lid 404 is positioned such that when the slider 413 and the holder 414 are located upwardly of the urine analyzing device 4, access can be gained to the holder 414 through the hole that is opened by the lid 404.

An electric motor 415 is mounted in the frame 411 for driving a timing belt 416 that runs parallel to the guide rails 412 and that is positioned alongside of one of the guide rails 412. The timing belt 416 is operatively coupled to the slider 413. When the motor 415 is energized, the urine test paper piece 6 held by the holder 414 is vertically moved between the urine reservoir 1e and the urine analyzing device 4.

The slider 413 and the holder 414 are partly enclosed by a cover 420 which is extensible and contractable as the slider 413 and the holder 414 are vertically moved. The cover 420 comprises three telescopic members 421, 422, 423 each in the form of a channel. The first member 421 is fixed to the frame 411. The second member 422 is smaller than the first member 421 so that the second member 422 can be accommodated in the first member 421, and the third member 423 is smaller than the second member 422 so that the third member 423 can be accommodated in the second member 422. When the slider 413 is lifted, the holder 414 is also lifted with the third member 423, which is gradually placed into the second member 422. Further upward movement of the slider 413 causes the second member 422, with the third member 423 accommodated therein, to be accommodated in the first member 421 until finally the second and third members 422, 423 and the holder 214 are fully positioned in the first member 421. At this time, the cover 420 is fully contracted as indicated by the solid lines in FIG. 4. Conversely, when the slider 413 is lowered, the holder 414 is also lowered with the third member 423 which descends out of the second member 422, and the first member 214 is also displaced downwardly out of the second member 422. Finally, the cover 420 is fully extended, covering the slider 413 and the holder 414 as indicated by the imaginary lines in FIG. 4. When the holder 414 is in its lowermost position directly above the urine reservoir 1e in order to apply a urine sample to the urine test paper piece 6 for analysis or to discard the urine test paper piece 6 after analysis, the holder 414 remains covered with the cover 420. Therefore, the holder 414 or the urine test paper piece 6 held thereby are prevented from being contaminated by water droplets or feces. While the cover 420 is composed of the three telescopic members, it may be composed of any number of telescopic members insofar as at least the uppermost member can accommodate the other members when contracted.

As shown in FIG. 5, the holder 414 comprises a small block having a vertical test paper insertion slot 435 and a horizontal slot 436 communicating transversely with the test paper insertion slot 435 and opening at the rear side of the holder 414. The holder 414 also includes a pair of L-shaped levers 437, 438 disposed in the horizontal slot 436 and pivotally supported by a pivot shaft 439. The levers 437, 438 are spaced from each other transversely with respect to the holder 414 (i.e., in the direction normal to the sheet of FIG. 5). The levers 437, 438 have rear ends projecting from the rear surface of the holder 414. The projecting rear ends of the levers 437, 438 protrude upwardly when their front ends in the test paper insertion sot 436 are engaged by a side of the urine test paper piece 6 which is inserted into the test paper insertion slot 435. Behind the holder 414, there are disposed two sensors $S_1$, $S_2$ associated respectively with the levers 437, 438. The sensors $S_1$, $S_2$ are turned off when the rear ends of the levers 437, 438 are lowered and turned on when the rear ends of the levers 437, 438 protrude upwardly. The sensors $S_1$, $S_2$ are electrically connected to the display panel 10.

As shown in FIG. 6, the urine test paper piece 6 comprises a water-soluble base 620 such as filter paper, a water-impermeable thin film 621 such as a resin film attached to a lower edge of the base 620 on one surface thereof, and a plurality of small patches 622 attached to the thin film 621 at spaced intervals, the small patches 622 being impregnated with respective urine-analyzing reagents. The reagents develop different colors depending on either the constituents (such as glucose, albumin, urobilinogen, occult blood, etc.) of the urine sample attached thereto or the concentrations of these constituents. The base 620 has a wider upper portion and two positioning holes 623 disposed below the wider upper portion. One side 624 of the wider upper portion of the base 620 is not recessed or cut away, but the other side 625 thereof has a recess 626. Thus, the opposite sides of the wider upper portion of the base 620 are asymmetrical in shape.

When the urine test paper piece 6 is properly inserted in the holder 414, the small reagent patches 622, to which the urine sample will be applied, face the front side of the urine analyzing device 4. If the urine test paper piece 6 is inserted with the patches 622 facing away from the urine analyzing device 4, the lever 437 is engaged by the side 624 of the urine test paper piece 6, and has its rear end protruding upwardly, turning the sensor $S_1$ on. At the same time, the lever 438 is positioned in the recess 626 in the other side 625 and engaged by the front wall of the test paper insertion slot 435, and has its rear end lowered, turning the sensor $S_2$ off. The output signals from the sensors $S_1$, $S_2$ at this time indicate that the urine test paper piece 6 has been inserted erroneously with the right side facing away from the urine analyzing device 4, and the display panel 10 may give the user a warning alarm such as warning sound or light. If the urine test paper piece 6 is inserted properly, the lever 437 is positioned in the recess 626 and its lower end is lowered, turning the sensor $S_1$ off, and the other lever 438 is engaged by the side 624 and its rear end protrudes upwardly, turning the sensor $S_2$ on. The output signals from the sensors $S_1$, $S_2$ now indicate that the urine test paper piece 6 has been inserted properly, and the display panel 10 may indicate the proper insertion to the user. If both the sensors $S_1$, $S_2$ are turned off, the output signals thereof indicate that no urine test paper piece 6 has been inserted, and the display panel 6 may give an indication to that effect. FIG. 7 is a table showing the sensor signal combinations and corresponding indications about how the urine test paper piece 6 has been inserted in the holder 414.

Since the reagents on the urine test paper piece 6 should not be contacted by water, it is preferably placed in a package. For use, the package is torn away, the lid 404 is opened, and the urine test paper piece 6 is inserted into the holder 414, all by the user. However, because the user is not an expert and cannot judge which side of the urine test paper piece 6 is the proper side, the user may insert the urine test paper piece 6 into the holder 414 with the colored reagent patches 622 facing away from the urine analyzing device 4, making it impossible for the urine analyzing device 4 to analyze the urine sample. With the above arrangement of the present invention, the urine test paper piece 6 is of an asymmetric shape such that the lever mechanism 437, 438 of the holder 414 will be differently positioned when it is engaged by the face and back of the urine test paper piece 6. Such different conditions are detected by the sensors $S_1$, $S_2$ in order to determine which side of the urine test paper piece 6 faces the urine analyzing device 4. If the urine test paper piece 6 is inserted erroneously, the display panel 10 can give the user a warning alarm, indicating that the urine test paper piece 6 should be inserted again.

In the above embodiment, two sensors are employed to detect the face and back of the urine test paper piece 6. However, the urine test paper piece 6 may be marked or punched in any area except the center thereof, and a single light sensor may be used for detecting the mark or hole for the detection of the face and back of the urine test paper piece 6.

Figure 8:
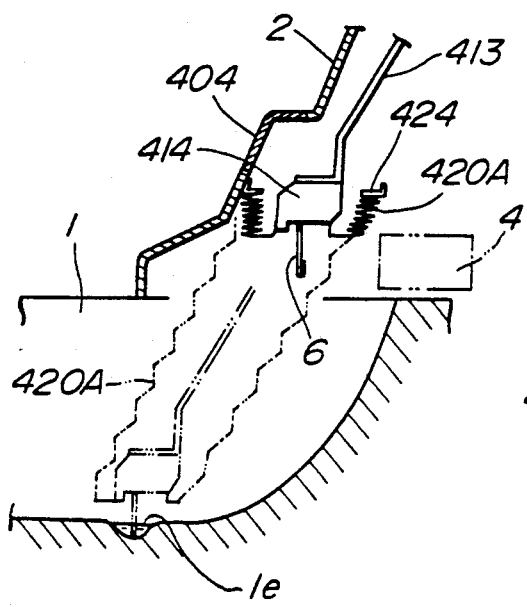
FIG. 8 is a side elevational view of a bellows-like cover according to a modification for a slider and a holder shown in FIG. 3.
Figure 9:
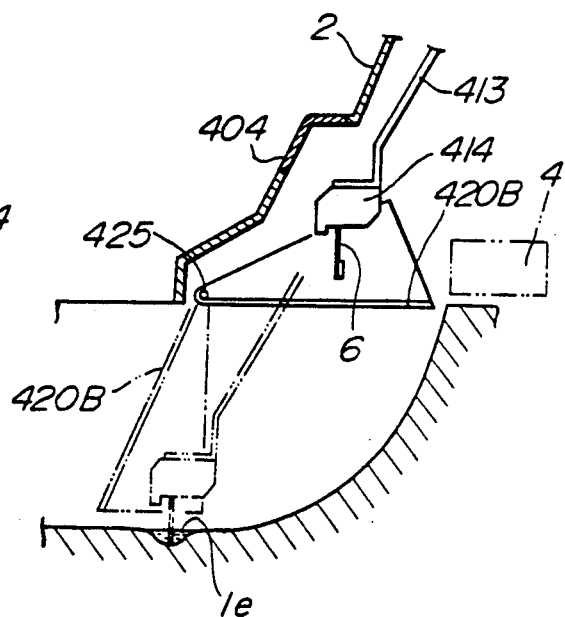
FIG. 9 is a side elevational view of a lid-like cover according to another modification for the slider and the holder shown in FIG. 3.
Figure 10:
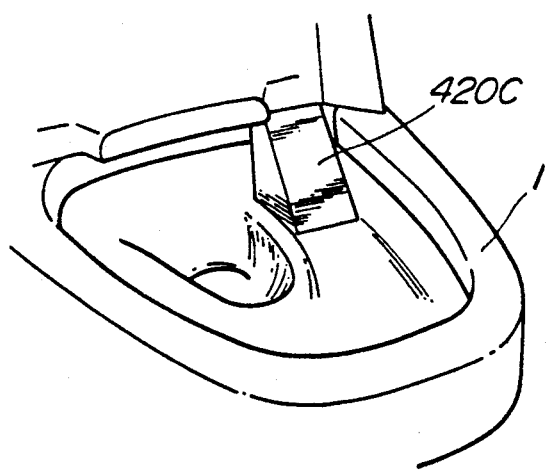
FIG. 10 is a perspective view of a box-like cover according to yet another modification for the slider and the holder shown in FIG. 3.

FIGS. 8 through 10 show modified covers for the slider 413 and the holder 414 of the lifting/lowering mechanism shown in FIGS. 3 and 4.

FIG. 8 shows a bellows-like cover 420A of an integral construction which has an upper end fastened to a bracket 424 in the box 2 and a lower end fixed to the holder 414. As the holder 414 is vertically moved by the lifting/lowering mechanism 400, the bellows-like cover 420A is extended and contracted while covering the slider 413 and the holder 414 at all times.

FIG. 9 shows a lid-like cover 420B which is supported for swinging movement about a shaft 425 on a lower portion of the box 2. The cover 420B is normally urged upwardly by a spring (not shown) to close an opening in the bottom of the box 2. When the holder 414 moves downwardly, the cover 420B is engaged by the holder 414 and turned downwardly about the shaft 425, thereby covering the slider 413 and the holder 414.

FIG. 10 shows a cover 420c comprising a box-like member attached to the bottom of the box 2 in covering relation to the entire path of the slider 413 and the holder 414 as they move vertically. The cover 420c is immovable and may conveniently be replaced with a new cover from time to time.

Figure 11:
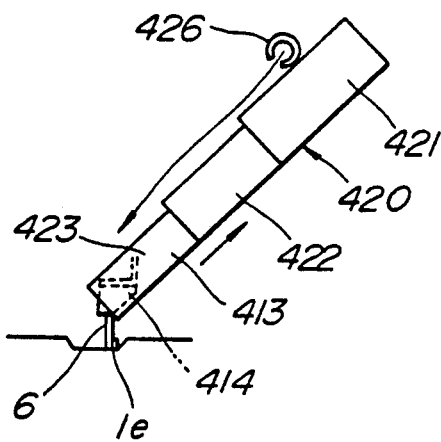
FIG. 11 is a side elevational view of the cover shown in FIG. 3 with a washing tube attached.

The covers shown above are used to prevent the slider 413 and the holder 414 from being contaminated. The cover 420 itself may be washed by a washing pipe 426 (FIG. 11) disposed on an upper front surface of the cover 420. The cover 420 can automatically be washed by a washing solution which is supplied from the washing tube 426 over the front surface of the cover 420 when necessary.

Since the holder 414 which holds the urine test paper piece 6 and the lifting and lowering mechanism for lifting and lowering the holder 414 are covered with the cover 420, the holder and the lifting and lowering mechanism are prevented from being contaminated by feces, and also from malfunctioning.

A shutter mechanism which is constructed like a combination of the cover 420 shown in FIGS. 3 and 4 and the cover 420B shown in FIG. 9 will now be described with reference to FIGS. 12 and 13.

Figure 12:
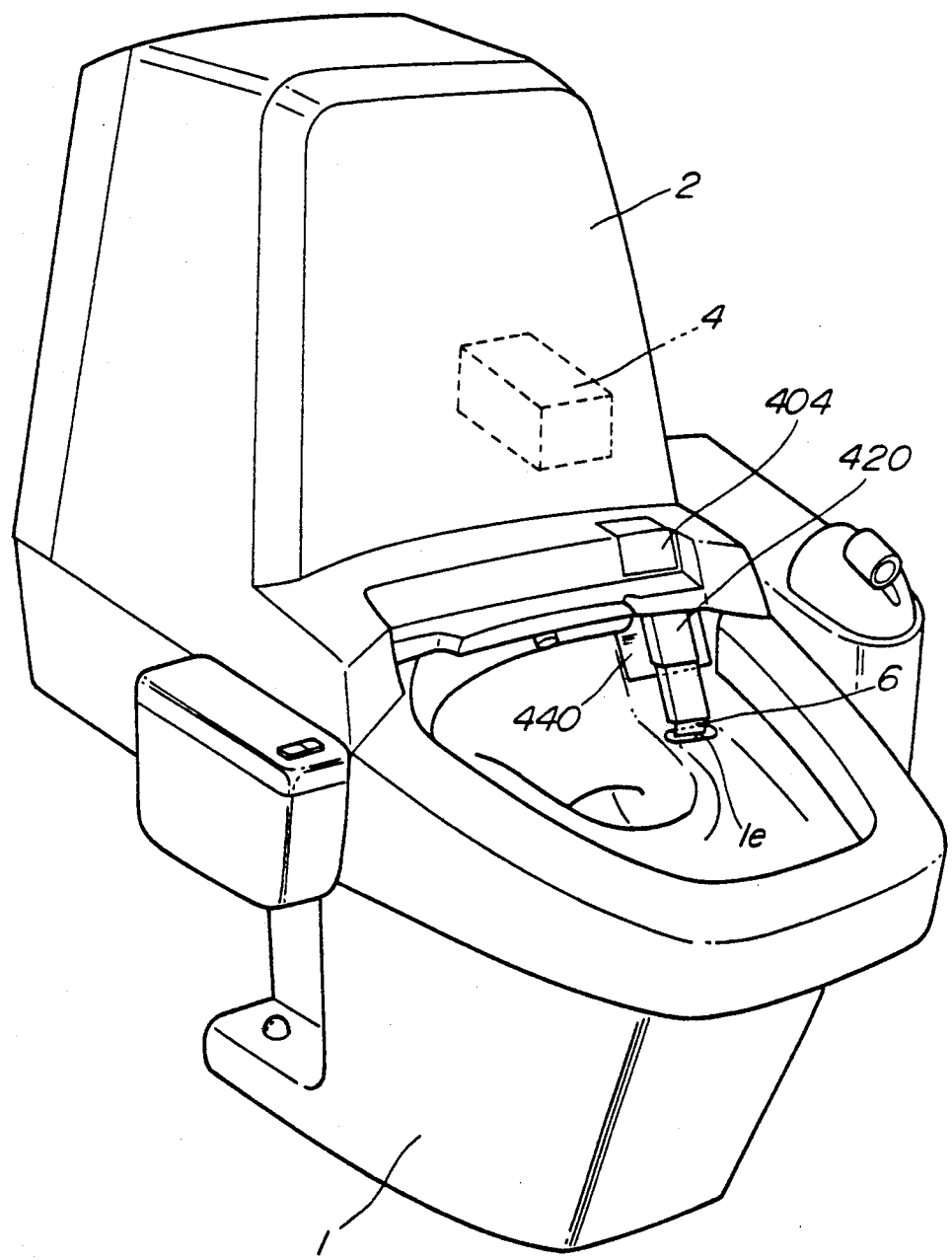
FIG. 12 is a perspective view of a toilet with a cover mechanism combined with the lifting/lowering mechanism shown in FIG. 3.
Figure 13:
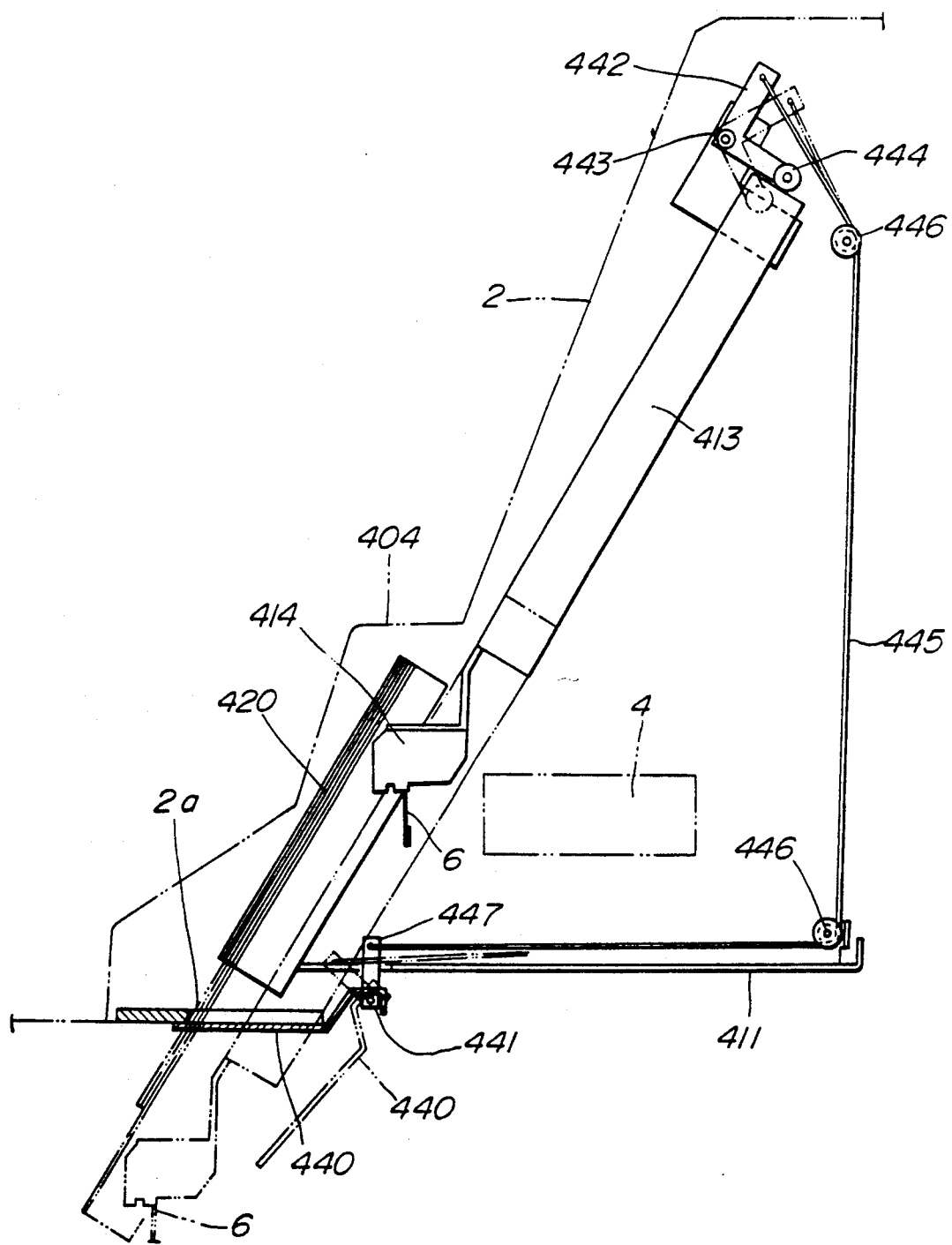
FIG. 13 is a schematic side elevational view of the cover mechanism shown in FIG. 12.

As shown in FIGS. 12 and 13, the box 2 has an outlet opening 2a defined in its bottom which is disposed above a rear portion of the bowl surface 1d of the toilet 1, the outlet opening 2a serving to pass therethrough the slider 413 as it is vertically moved by the lifting and lowering mechanism 400. A shutter 440 is swingably attached in covering relation to the outlet opening 2a by a shaft 441. An L-shaped lever 442 is swingably supported in an upper end portion of the frame 411 by a shaft 443, and a roller 444 mounted on one end of the lever 442 is held against the upper end of the slider 413. The other end of the lever 442 is coupled to one end of a wire 445 which extends around a guide roamer 446 mounted in the frame 411. The other end of the wire 445 is fastened to a lever 447 which is connected to the shutter 440.

When the slider 413 is lifted to its uppermost position, the roller 444 is pushed upwardly by the upper end of the slider 413, causing the lever 442 to swing about the shaft 443 to the solid-line position in FIG. 13. The wire 445 is now pulled upwardly to turn the shutter 440 clockwise about the shaft 441, thereby closing the opening 2a.

At this time, the lid 404 of the box 2 may be manually opened, and the urine test paper piece 6 may be manually inserted into the holder 414 on the lower end of the slider 413.

After the urine test paper piece 6 has been inserted, the motor 415 is energized to lower the slider 413. Since the lever 442 is normally urged to turn clockwise by the weight of the shutter 440, the lever 442 now turns to the imaginary-line position in FIG. 13, and hence the shutter 440 turns to the imaginary-line position, thereby opening the opening 2a.

The slider 413 and the holder 414 can now be lowered through the opening 2a to the urine reservoir 1e on the bowl surface 1d. At the same time that the slider 413 and the holder 414 are lowered, the cover 420 is extended downwardly through the opening 2a to prevent the slider 413 and the holder 414 from being contaminated by feces.

After a urine sample in the urine reservoir 1e has been attached to the lower end of the urine test paper piece 6, the motor 415 is reversed to lift the slider 413 to move the urine test paper piece 6 held by the holder 414 up to a position in front of the urine analyzing device 4, as shown in FIG. 13. Since the slider 413 is lifted again to the upper limit position at this time, the lever 442 is turned counterclockwise, pulling the wire 445 to close the opening 2a with the shutter 440.

While the urine test paper piece 6 held by the holder 414 is being held at rest in the box 2, water on the bowl surface 1d tends to evaporate and the vapor would flow upwardly through the opening 2a, reaching the reagents on the urine test paper piece 6. Therefore, the opening 2a should be closed by the shutter 440 to protect the urine test paper piece 6 and also the urine analyzing device 4 from moisture. When the urine test paper piece 6 is moved toward the front face of the urine analyzing device 4 for optical analysis of the urine sample accurately, the interior space of the box 2 should be kept dark. This requirement can be met by the shutter 440 which, when closed, reliably renders the interior space of the box 2 dark.

Figure 14:
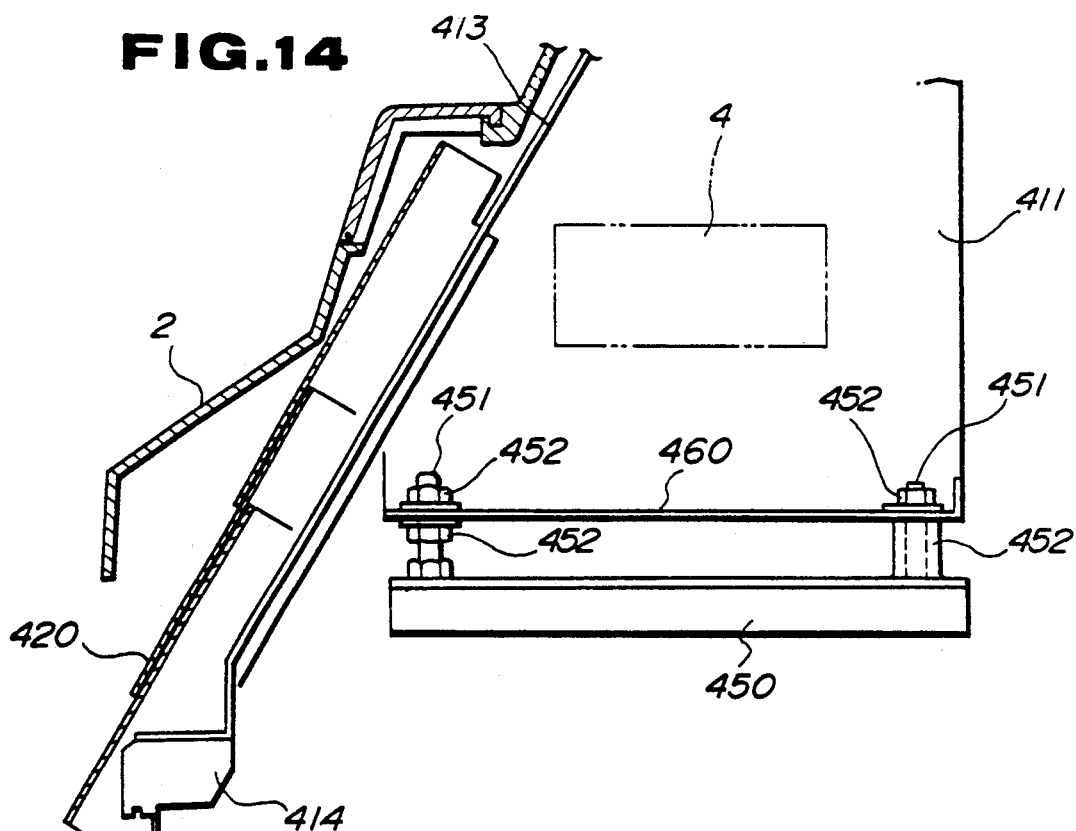
FIG. 14 is a cross-sectional view of a frame of the lifting/lowering mechanism shown in FIG. 3.
Figure 15:
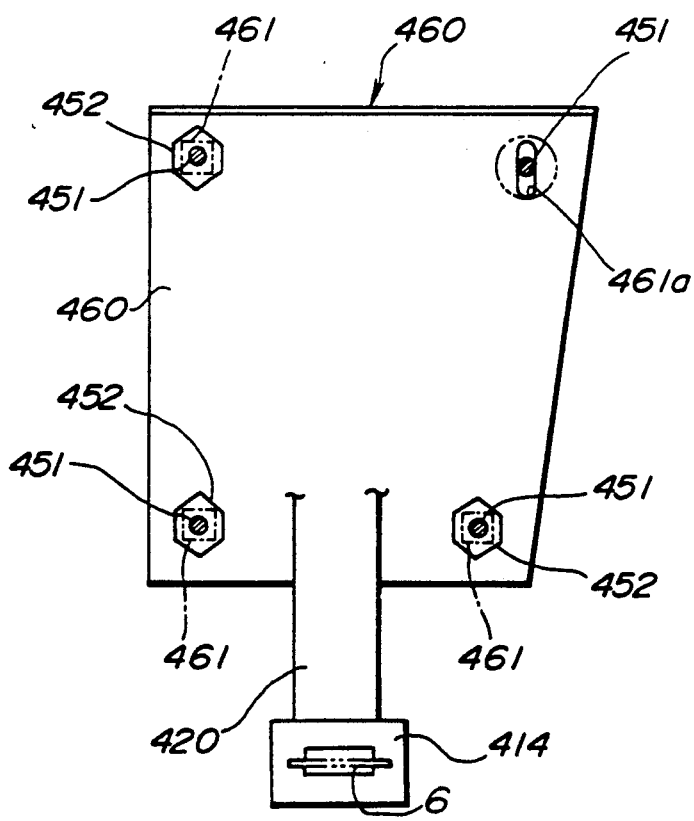
FIG. 15 is a plan view of the frame shown in FIG. 14.

The frame 411 of the lifting and lowering mechanism 400 is mounted on a base plate which is positioned rearwardly and upwardly of the toilet 1 or a base plate which is positioned within the box 2 behind the toilet 1. More specifically, the lifting and lowering mechanism 400 is required to be mounted on a fixed base plate which is stable with respect to the toilet 1 in order to move the urine test paper piece 6 reciprocally between the urine reservoir 1e and the urine analyzing device 4 in the box 2. The toilet 1 and/or the box 2 is low in dimensional accuracy as they are manufactured by casting a slip and firing the cast product. When the lifting and lowering mechanism 400 is to be fixed to the toilet 1 or the like, it is necessary to position the lifting and lowering mechanism 400, particularly the parallel rails 412, accurately with respect to the urine reservoir 1e. If the lifting and lowering mechanism 400 were not accurately positioned with respect to the urine reservoir 1e, then the urine test paper piece 6 lowered by the lifting and lowering mechanism 400 might be displaced from the urine reservoir 1e. FIGS. 14 and 15 show a frame 411 which can easily absorb manufacturing dimensional errors of the toilet 1 or the like, allowing the lifting and lowering mechanism 400 to be installed on a base plate fixed with respect to the toilet 1.

As shown in FIG. 14, the frame 411 of the lifting and lowering mechanism 400 is mounted on a base plate 450 which is fixed to the toilet 1 above the urine reservoir 1e. Bolts 451 are vertically mounted on the upper surface of the base plate 450 at respective four corners thereof. The frame 411 has a horizontal bottom plate 460 which has insertion holes 461 defined respectively in four corners thereof. For attachment the bolts 451 are inserted respectively through the insertion holes 461 in the bottom plate 460, and two nuts 452 are tightened over each of the bolts 451 above and below the bottom plate 460, thus affixing the frame 411 to the base plate 450. As shown in FIG. 15, one of the insertion holes 461 in the base plate 450 comprises an oblong hole 461a, and the other three insertion holes 461 comprise square holes which are sufficiently larger than the diameter of the bolts 451.

If the urine test paper piece 6 is displaced from the urine reservoir 1e due to manufacturing errors of the toilet 1 when the slider 413 is slid down the parallel rails 412 to the lowermost position, then the nuts 452 which fasten the frame 411 to the base plate 450 are loosened, and the frame 411 is jiggled up and down, laterally, or to and from within a range allowed by the clearances between the bolts 451 and the insertion holes 461, so that the frame 411 is positionally adjusted. Thereafter, the nuts 452 are retightened to fix the frame 411 to the base plate 450.

Therefore even if the toilet 1 has manufacturing errors which make the lifting and lowering mechanism 400 or the parallel rails 412 positionally misaligned with respect to the urine reservoir 1e, such manufacturing errors can easily be absorbed as the frame 411 can easily be positionally adjusted with respect to the toilet 1.

With the toilet device described above, the urine reservoir 1e may be formed simply by modifying a portion of the bowl surface 1d while keeping the entire original shape of the bowl surface 1d, and the lifting and lowering mechanism 400 is fully accommodated together with the slider 431 and the cover 420 within the box 2 which is disposed rearwardly and upwardly of the toilet 1. For urine examination, the slider 413 is moved forwardly and downwardly from the bottom (outlet opening 2a) of the box 2 toward the urine reservoir 1e that is located in a rear portion of the bowl surface 1d, and then moved back rearwardly and upwardly until the slider 413 is fully stored in the box 2. Therefore, the conventional toilet and toilet-related components are not required to be largely changed in design in reducing the present invention to practice. Particularly, the lifting and lowering mechanism 400, together with the slider 413 and the holder 420, are stored as toilet-related components compactly in the box 2.

A preferred embodiment of the display panel 10 shown in FIG. 1 will be described below with reference to FIGS. 16 through 19.

When a urine sample is to be analyzed or a blood pressure is to be measured using the toilet device according to the present invention, the user is required to operate various devices and mechanisms according to predetermined procedures. For example, for analyzing a urine sample, the user is required to urinate after a urine test paper piece 6 has been set in the holder 414. For blood pressure measurement, the user is required to insert a finger into the measuring cuff 8. If such operation procedures were written in small letters on a control panel which also carries many items of information, the user would have difficulty understanding the procedures quickly. Any required indications written by letters should therefore be kept to a minimum. Particularly, aged people tend to take time reading the letters, and also tend to misunderstand the operation procedures if the indications were given by only letters.

Accurate display of the proportions of constituents of an analyzed urine sample, typically in numerical values with accuracy up to the order of 1, may not be useful to the user. Indication of positive, false positive, or negative in small letters fails to give the user a clear visual image representing how good or bad his health conditions are.

According to the present invention, the display panel has an operation function allowing the user to operate the toilet device reliably without error according to operation procedures even if instructions written in small letters are not read for urine and blood pressure inspection. Also, the present display panel has a display function which not only displays the results of inspection by way of numerical values but also gives the user a visual image indicating how good or bad the user's health conditions are.

Figure 16:
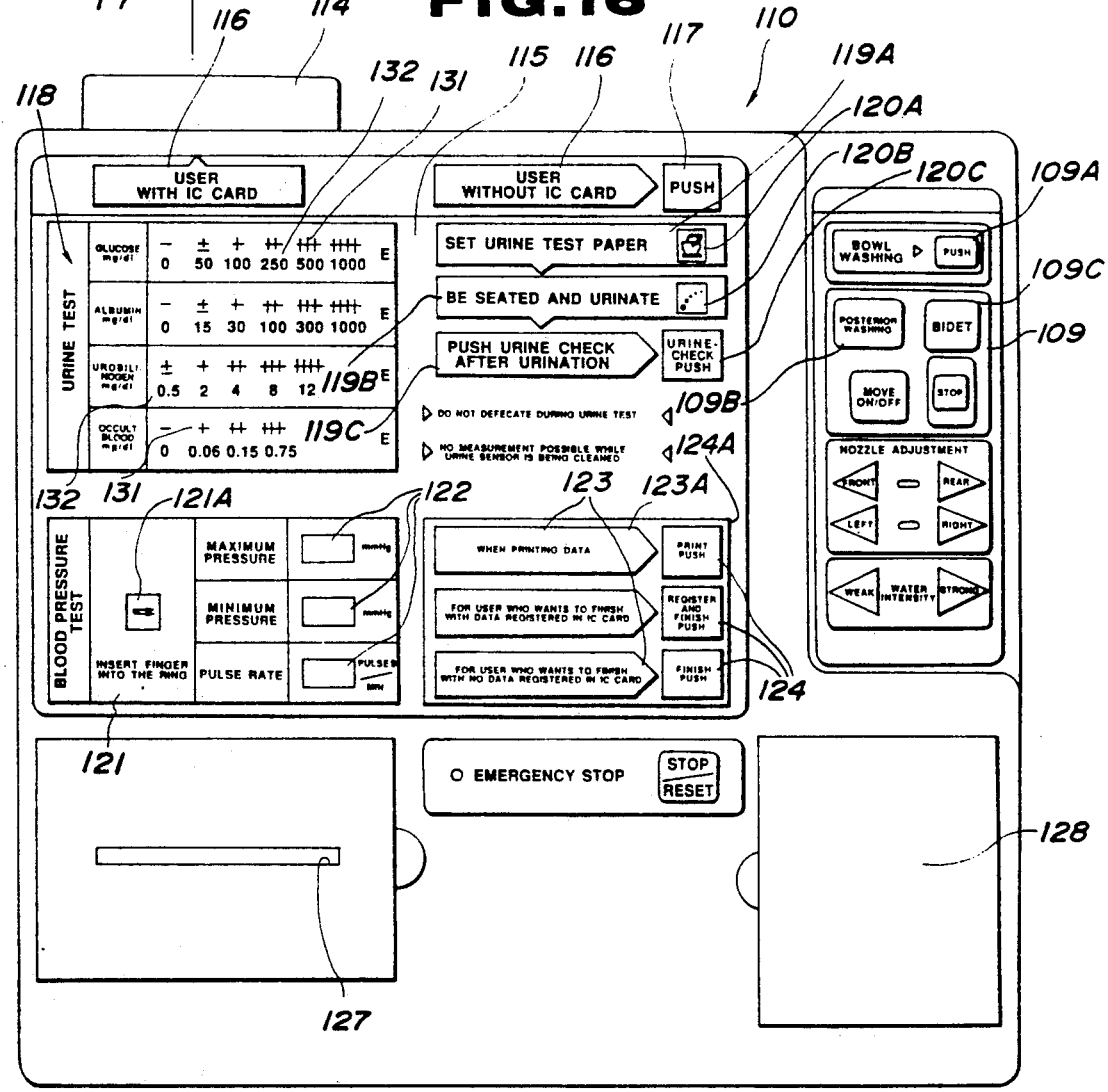
FIG. 16 is a front elevational view of a display panel of the toilet device according to the present invention.
Figure 17:
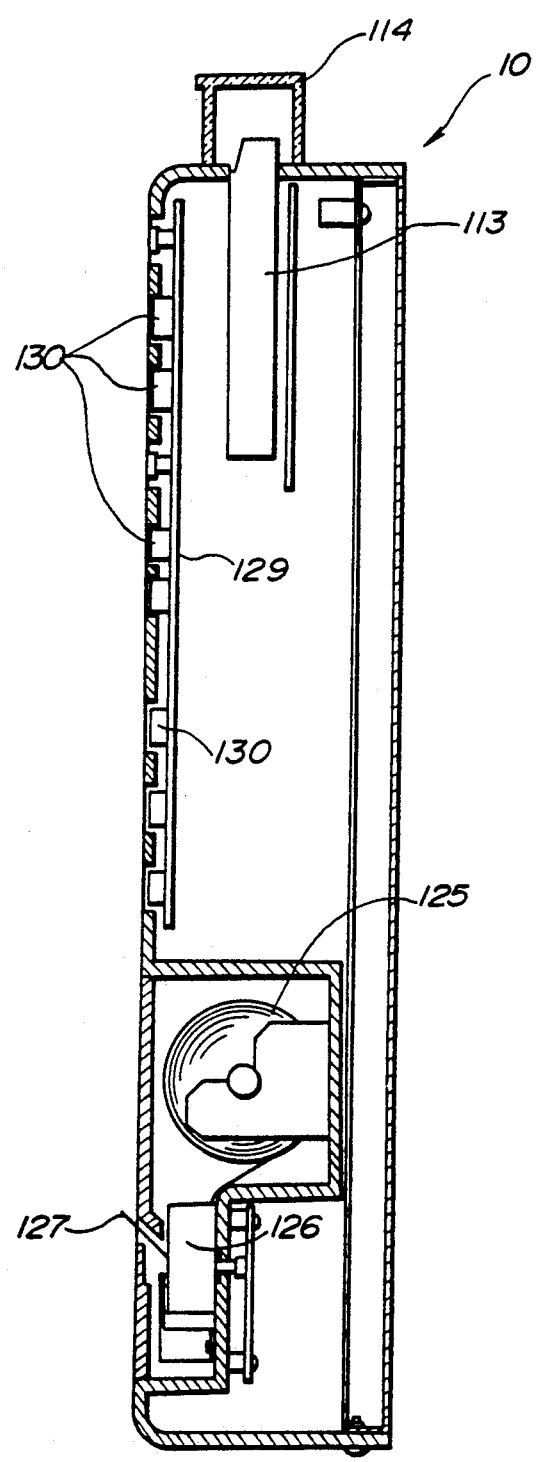
FIG. 17 is a cross-sectional view taken along line 17—17 of FIG. 16.
Figure 18A:
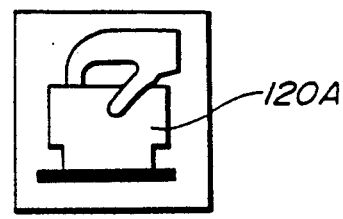
FIGS. 18A, 18B, and 18C are enlarged views of symbols on the display panel shown in FIG. 16.
Figure 18B:
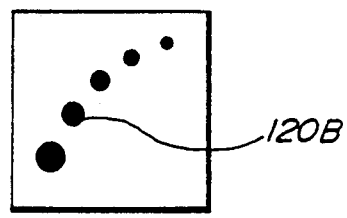
Figure 18C:
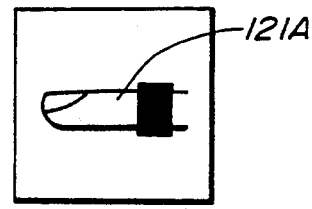

As shown in FIGS. 1, 16, and 17, the display panel 10 has in its upper wall an insertion slot 112 for an IC card 111 which stores the user's name and past health data. As shown in FIG. 17, a card reader/writer 113 is disposed below the insertion slot 112 in the display panel 10. The insertion slot 112 is covered with a transparent cover 114 which prevents dust and water from entering the display panel 10 through the insertion slot 112. The transparency of the cover 114 allows the user to see the inserted IC card 111, so that the user will not forget to remove the inserted IC card 111 from the insertion slot 112.

A transparent or semitransparent plate 115 is mounted on the front surface of the display panel 10, for displaying various indications.

More specifically, as shown in FIG. 16, the plate 115 bears instructive sentences 116 for user with and without IC cards and a switch 117, on upper left and right portions thereof.

The plate 115 also includes a display area 118 for indicating the results of a urine analysis or examination, the display area 118 extending downwardly from the upper left portion of the plate 115, and an instructive area 119 indicating operation procedures for a urine analysis and an indication area 120 for the operation procedures, the instructive and indication areas 119, 120 being positioned on the righthand side of the display area 118. The indication area 120 includes symbols which gives the user visual images of indications given by the indication area 120. More specifically, the instructive area 119 includes an instructive sentence 119A for instructing the user to set a urine test paper piece 6 in the holder, and the indication area 120 includes a symbol indication 120A (see FIG. 18A) adjacent to the instructive sentence 119A, the symbol indication 120A representing a simplified image of the setting of the urine test paper piece 6. The instructive area 119 also includes an instructive sentence 119B for instructing the user to be seated on the seat 1b and urinate, and the indication area 120 includes a symbol indication 120B (see FIG. 18B) adjacent to the instructive sentence 119B and representing a simplified image of the urination. The instructive area 119 further includes a final instructive sentence 119C for instructing the user to effect a urine analysis or examination (with the lifting and lowering mechanism 400 and the urine analyzing device 4) after the urination, and the indication area 120 further includes a switch 120C for starting the urine analysis, the switch 120C being positioned adjacent to the instructive sentence 119C. The switch 120C may bear a symbol indication which represents the urine analysis.

As shown in FIG. 17, light-emitting elements 130 are disposed behind the respective symbol indications 120A, 120B and the switch 120C, so that the symbol indications 120A, 120B and the switch 120C can be illuminated with a view to guiding the user to follow the operation procedures properly.

If the user has operated the display panel 10 several times in the past, he first visually observes only the symbol indication 120A associated with the instructive sentence 119A and sets the urine test paper piece 6. Even if the user is not used to the display panel 10, he can easily understand that the instructive sentence 119A should be followed prior to the instructive sentence 119B because the former is positioned above the latter, and can easily understand the operation procedure simply by reading the instructive sentence 119A. After the urine test paper piece 6 has been set in the holder, since the symbol indication 120B associated with the instructive sentence 119B is illuminated giving the user an image of urination, the user is instructed to urinate. Thereafter, the user pushes the switch 120C.

When the switch 120C is pushed, a signal is sent through the communication cable from the display panel 10 to the toilet device, and the lifting and lowering mechanism 400 is actuated to lower the urine test paper piece 6 into the urine reservoir 1e. After the urine test paper piece 6 has been immersed in the urine sample in the urine reservoir 1e, the urine test paper piece 6 is lifted by the lifting and lowering mechanism 400 and brought into a position in front of the urine analyzing device 4. The results of a urine analysis effected on the urine sample by the urine analyzing device 4 are delivered through the communication cable to the display area 118, which then displays corresponding indications.

The plate 115 also includes, below the display area 118, an instructive sentence 121 for starting to examine a blood pressure and a symbol indication 121A (see FIG. 18C) representing an image of the blood pressure examination, and indication areas 122 for indicating a maximum blood pressure, a minimum blood pressure, and a pulse rate. A light-emitting element is also positioned behind the symbol indication 121A. When the user visually confirms the illumination of the symbol indication 121A, the user inserts a finger into the cuff 8, whereupon a blood pressure measuring device or mechanism is actuated to measure the blood pressures and pulse rate of the user. The measured blood pressures and pulse rate are sent over the communication cable to the display panel where they are displayed in the indication areas 122. The symbol indication 121A may double as a pushbutton switch so that it starts the measurement of blood pressures when pushed.

The plate 115 also has, below the instructive area 119, instructive sentences 123 to be referred to after the examination is finished, and switches 124 corresponding to the instructive sentences 123. When a print switch 124A, for example, adjacent to an instructive sentence 123A is pushed, the results of the urine analysis and the results of the blood pressure measurement are printed out through a slit 127 in the display panel 10.

The display panel 10 has a recess defined in a righthand portion of the front surface thereof. A remote control panel 109 for remotely controlling the local region washer 5 is disposed in the recess. The remote control panel 109 includes a bowl washing switch 109A for starting to wash the toilet bowl 1d. As shown in FIG. 17, the display panel 10 houses, in a lefthand lower portion thereof, a roll 125 of paper, a printer 126 for printing the results of a urine analysis and the results of a blood pressure measurement on the roll 125 of paper, and the slit 127 for discharging the printed paper from the roll 125. The display panel 10 also includes a storage chamber 128 for storing pieces 6 of urine test paper, the storage chamber 128 being positioned in a righthand lower portion of the display panel 10.

Figure 19:
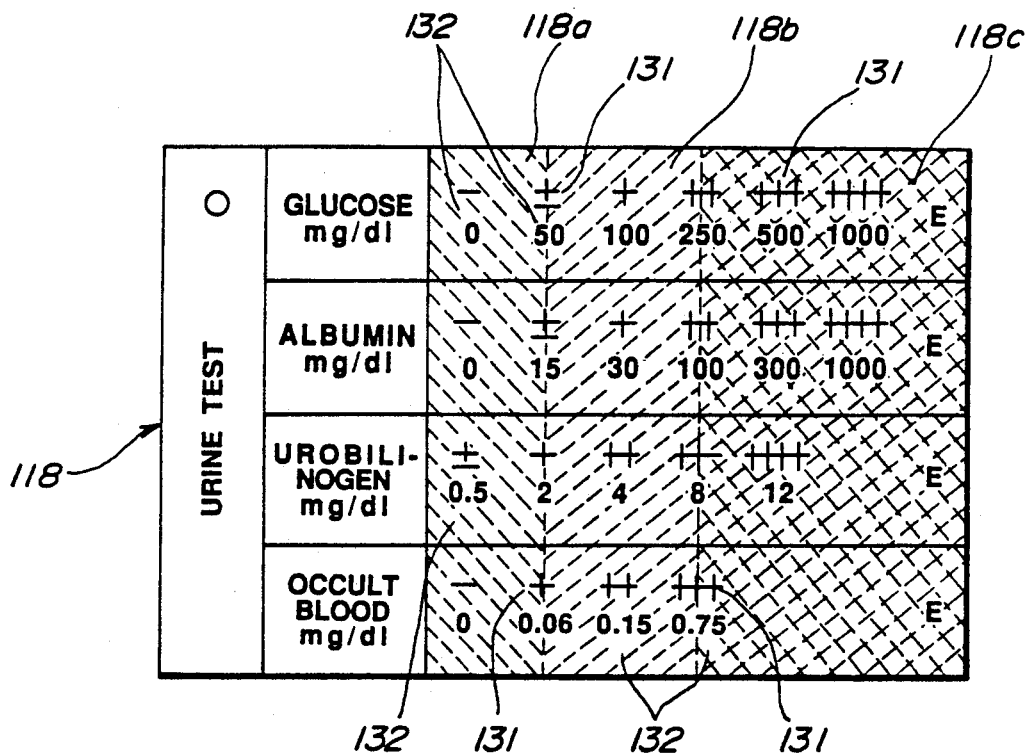
FIG. 19 is an enlarged view of a display unit for displaying the results of a urine test on the display panel shown in FIG. 16.

The display area 118 for displaying the results of a urine analysis includes four vertically divided sections for displaying the amounts of constituents (glucose, albumin, urobilinogen, and occult blood) of a urine sample to be analyzed, as also shown in FIG. 19. Each of the sections includes a plurality of marks 131 indicating health data in steps, and a plurality of quantitative values 132 corresponding to the marks 131. These marks 131 and quantitative values 132 are illuminated at respective steps by light-emitting elements disposed therebehind. The marks 131 include "−" signs representing negative and "+" signs representing positive. As more signs "+" are indicated, the positive degree of the results increases.

In order for the user to immediately understand his health conditions upon seeing the displayed results, a region 118a in the display area 118 should preferably be colored with blue or green, a region 118b with yellow or orange, and a region 118c with red or pink.

Since the results of a urine examination or analysis are indicated stepwise by the signs "−" and "+" rather than numerical values only, any users which may not have expert's knowledge can easily take care of their health in everyday life based on the indications on the display panel 10.

Figure 20:
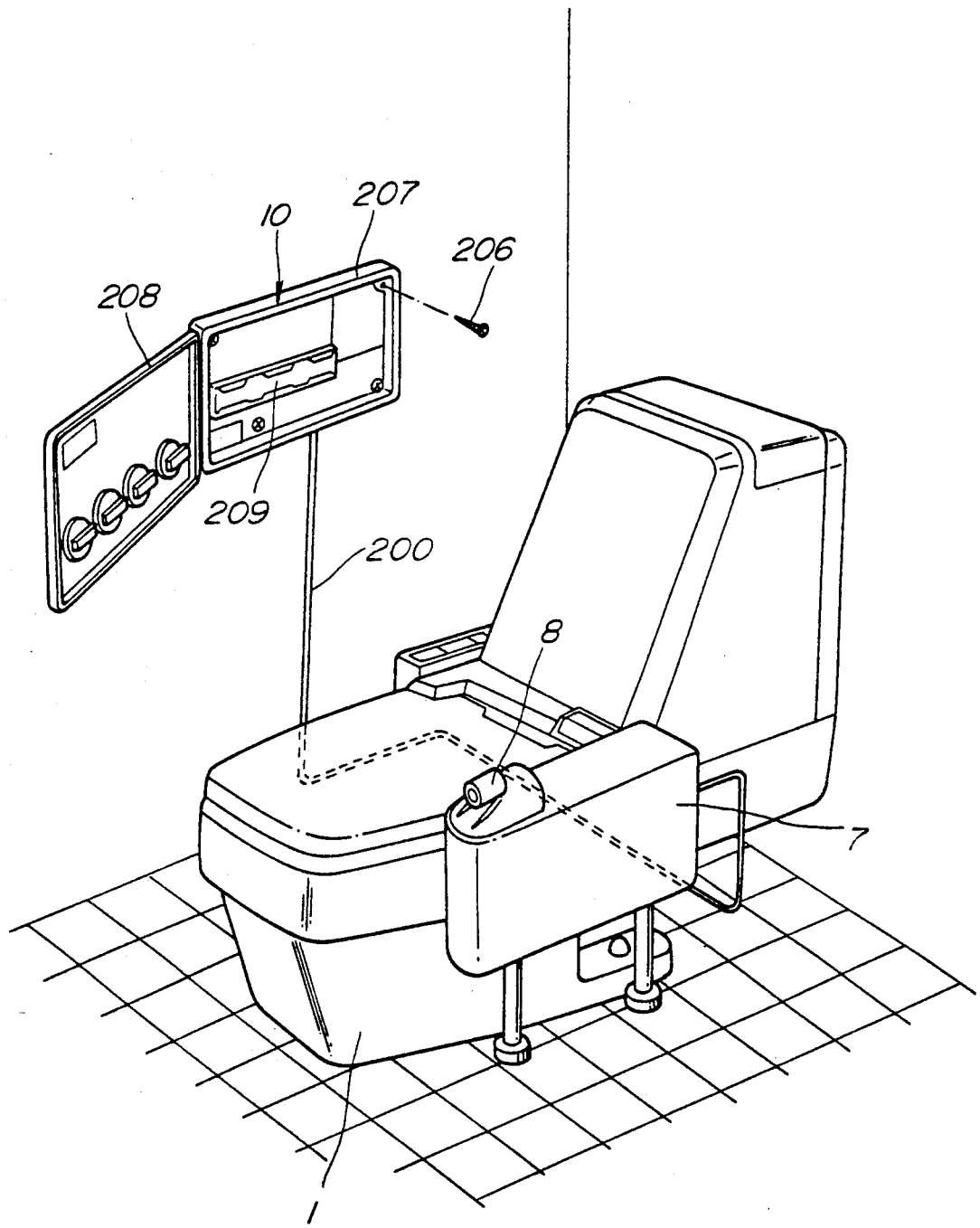
FIG. 20 is a perspective view of a toilet device in which the toilet and the display panel shown in FIG. 1 are connected by a communication cable.
Figure 21:
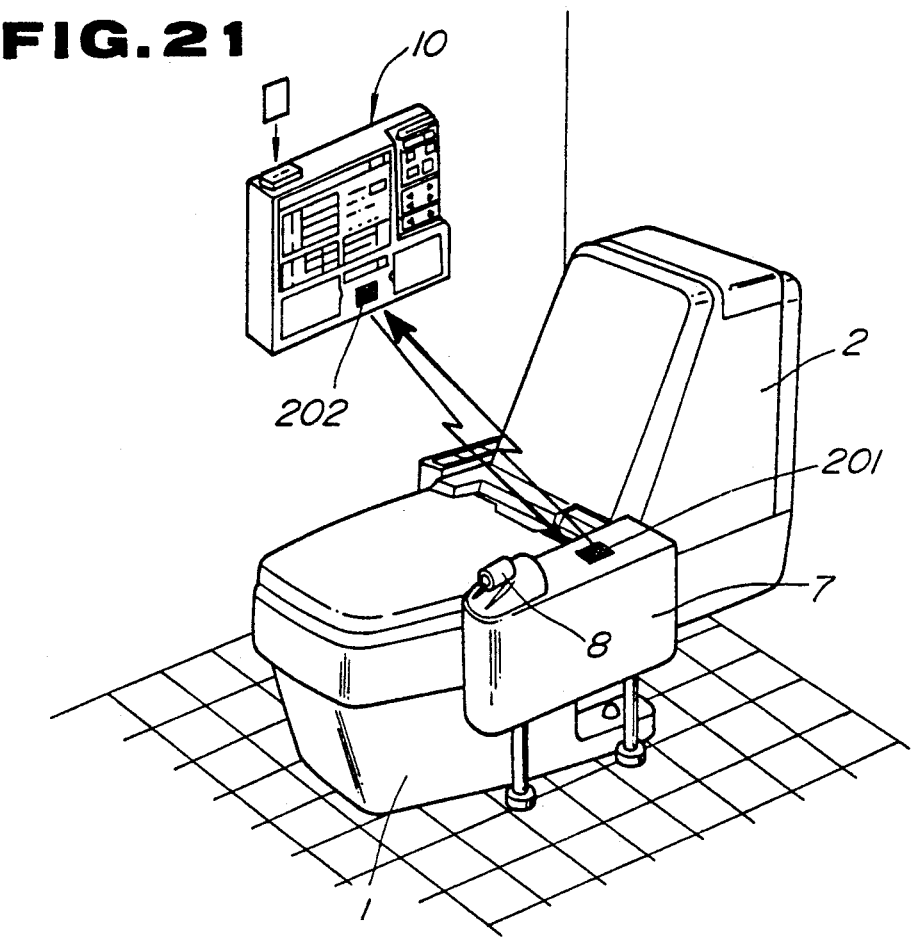
FIG. 21 is a perspective view of a toilet device in which the toilet and the display panel shown in FIG. 1 are connected by an optical communication link.

The display panel 10 is electrically connected to the blood pressure measuring equipment 7, 8 and the urine analyzing equipment 400, 4 through the communication cable, as described above. A control system for the blood pressure measuring equipment and the urine analyzing equipment may be disposed in the control box 7, and the control box 7 may be connected to the display panel 10 through a communication cable 200 as shown in FIG. 20. For attaching the display panel 10 to a wall, a lid 208 of the display panel 10 may be opened, and a display panel body 207 may be fastened to the wall by screws 206. The present invention is not limited to the above communication cable, but the display panel 10 and the control box 7 may be connected by an optical communication link utilizing infrared radiation. One example of such optical communication link is illustrated in FIG. 21. As shown in FIG. 21, an optical data transmitter and receiver unit 201 connected to the blood pressure measuring equipment and the urine analyzing equipment is mounted on an upper surface of the control box 7, and another optical data transmitter and receiver unit 202 connected to the display panel 10 is mounted on a lower front surface of the display panel 10. Optical control data and result data can be transmitted between the transmitter and receiver units 201, 202. The transmitter and receiver units 201, 202 may be located in any of other positions. Particularly, the transmitter and receiver 201 may be located on a side of the box 2 which faces the display panel 10. The optical communication link allows the display panel 10 to be positioned more freely with respect to the toilet device.

Figure 22:
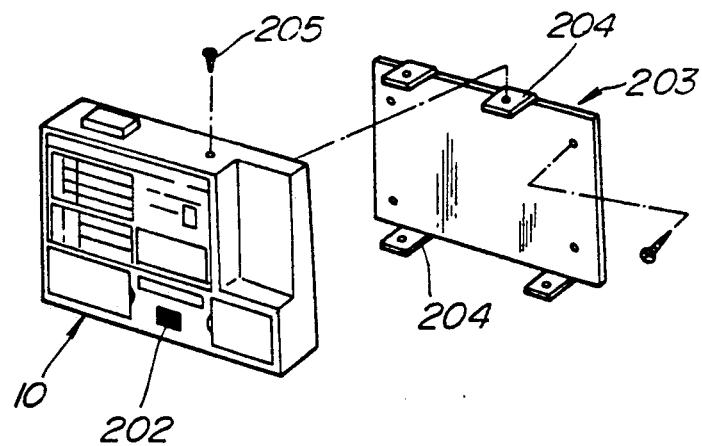
FIG. 22 is an exploded perspective view of a modified structure for attaching the display panel shown in FIG. 20 to a wall.

In the case where the display panel 10 is fastened to the wall by the screws 206 as shown in FIG. 20, a printed circuit board 209 in the display panel body 207 may be damaged by the screws 206. FIG. 22 shows an attachment arrangement designed to avoid such a drawback. As shown in FIG. 22, a case plate 203 which can fit with the rear side of the display panel 10 is first fastened to the wall by screws, and then the display panel 10 is fitted over bent pieces 204 of the case plate 203 and fastened to the case plate 203 by screws 205. With the attachment arrangement shown in FIG. 22, the printed-circuit board in the display panel 10 is not exposed and hence damaged when the display panel 10 is fastened to the wall, and the display panel 10 can easily be installed on the wall.

The toilet device according to the present invention can analyze a urine sample of the user and also simultaneously measure the blood pressure of the user, as described above with reference to the display pane 10. More specifically, as shown in FIG. 1, a hand rest 8a which includes the blood pressure measuring cuff 8 projects on the upper surface of the control box 7 which is located on the lefthand side of the toilet 1. The control box 7 serves as a control system for blood pressure measurements, incorporating a measuring instrument, a source of air under pressure, and a cylinder unit.

With the finger blood pressure meter positioned as shown in FIG. 1, since the finger is positioned below the heart of the user sitting on the seat 1b, the measured blood pressure value is higher than the actual blood pressure due to the head difference. To adjust the height level between the finger in the cuff 8 and the heart of the user, the control box 7 can be vertically moved along guide rods 7a by the cylinder unit in the control box 7. However, the cylinder unit and associated parts may be dispensed with to simplify the blood pressure measuring mechanism.

Figure 23:
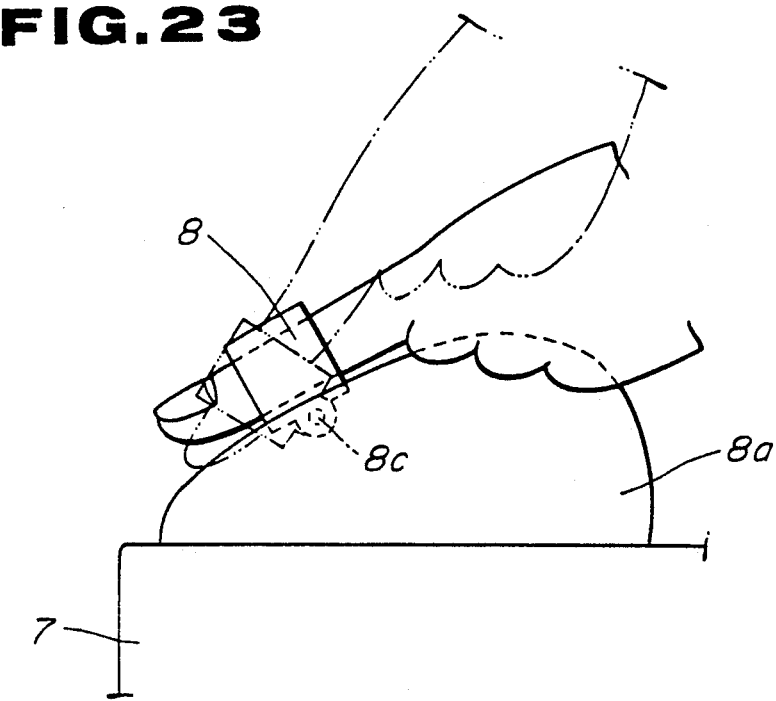
FIG. 23 is an enlarged side elevational view of a blood pressure measuring cuff in the toilet device shown in FIG. 1.

One preferred embodiment of the blood pressure measuring mechanism will be described with reference to FIGS. 1, 23, and 24.

As shown in FIG. 1, the cuff 8 in which the finger is inserted for the measurement of the blood pressure and pulse rate is disposed on the hand rest 8a on the upper surface of the control box 7. The hand rest 8a has a substantially semi-spherical shape so that a hand can snugly be placed thereon. The cuff 8 is positioned on a front downwardly inclined upper surface of the hand rest 8a, so that the finger can smoothly be inserted into the cuff 8. A double-layer band which can be inflated when supplied with air is mounted in the cuff 8 to prevent undue forces from being exerted on the inserted finger should the user inadvertently stand up. As shown in FIG. 23, the cuff 8 is pivoted to the hand rest 8a for angular movement about a shaft 8c in a certain vertical angular range. The vertical angular range in which the cuff 8 can swing is selected such that no undue forces are applied to the finger when the user stands up with the finger remaining in the cuff 8. It is preferable that any swinging movement of the cuff 8 be subjected to a small resistance because the cuff 8 would strongly hit the hand rest 8a at ends of its stroke without such a resistance. In FIG. 1, the hand rest 8a has guide ridges 8b for guiding the finger when it is inserted into the cuff 8.

When the user wishes to measure his blood pressure and/or pulse rate, the IC card 111 belonging to the user is inserted into the insertion slot 112 in the display panel 10. The card reader/writer 113 in the display panel 10 now reads the name, weight, height, sitting height of the user or the previous data of the user from the inserted IC card 111.

At the same time that the user inserts the IC card 111, the user is seated on the toilet 1, inserts a finger of his left hand into the cuff 8 coupled to the blood pressure measuring mechanism, and uses the right hand to turn on the switch on the display panel 10 to start a blood pressure measuring process, i.e., push the symbol indication 121A on the display panel 10. Alternatively, the cuff 8 may be combined with an automatic sensor which detects the insertion of a finger into the cuff 8 after the user is seated on the toilet 1. When the blood pressure measuring process is started, the double-layer band in the cuff 8 is supplied with air, strongly pressing the inserted air to temporarily stop the flow of blood in the finger. Then, the air is gradually removed from the double-layer band, and the blood pressure is measured as a maximum blood pressure when the blood starts to flow in the finger. When the air is completely removed from the double-layer band and the blood flow is normal, the blood pressure is measured as a minimum blood pressure.

Figure 24:
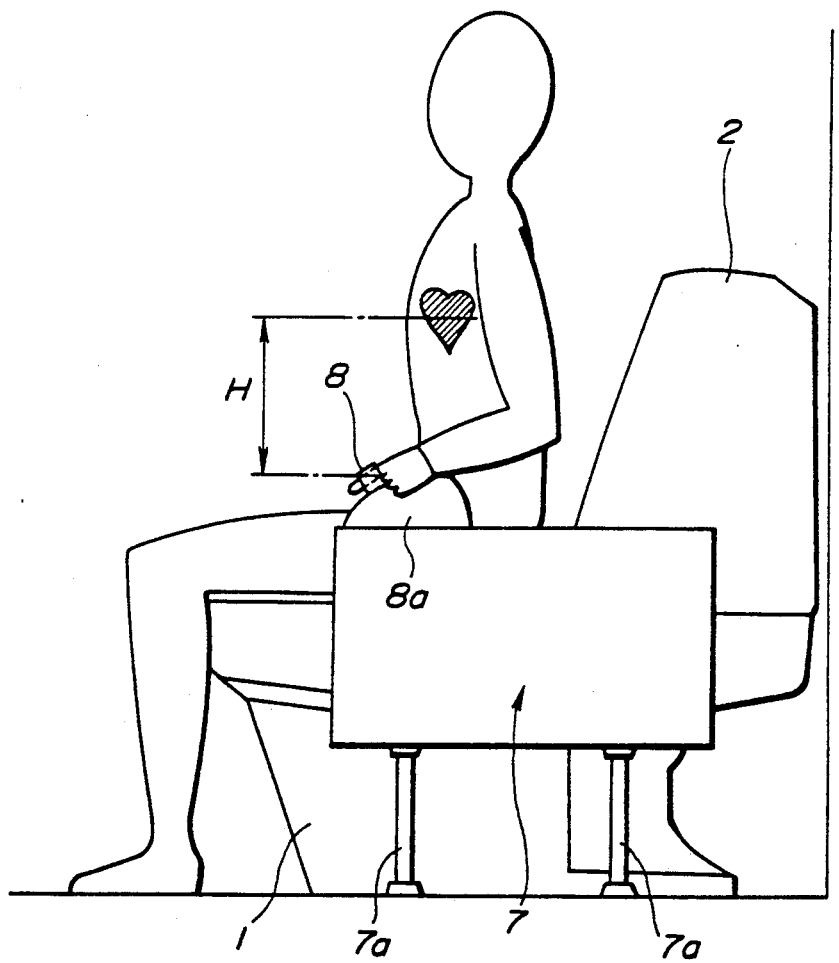
FIG. 24 is a side elevational view showing that a user is seated on the toilet shown in FIG. 1.

As shown in FIG. 24, the cuff 8 is lower than the heart of the user by a height H. Therefore, the measured blood pressure is higher than the actual blood pressure by the head difference corresponding to the height H. The measured values which are displayed on the indication areas 122 of the display panel 10 are corrected by compensating for the head difference H. The corrected values are calculated from the height or sitting height of the user, which is stored in the IC card 111.

However, since some users may not have IC cards, values calculated from a reference height may be used as corrected values for the compensation for the head difference H.

Even if the user inadvertently stands up while the finger 8 is being inserted in the cuff 8 after the blood pressure measurement, since the cuff 8 swings with the finger, no undue forces are applied to the finger, which is therefore protected from injury.

When the user wishes to examine his urine, the user has to push the switch 120C on the display panel 10 at suitable timing. More specifically, the final instructive sentence 119C in the instructive area 119 on the display panel 10 represents an instruction to enable the urine analyzing device 4 to examine or analyze the urine sample after urination. Unless the switch 120C is pressed after urination, the urine sample will not be analyzed or examined. If the switch 120C were pressed too early, the urine test paper piece 6 would be lowered into the urine reservoir 1e by the lifting and lowering mechanism 400 before urine is sampled in the urine reservoir 1e, and therefore, the urine test paper piece 6 would be lifted without any urine sample thereon, and the urine analyzing device 4 would start a urine analysis without any urine sample. Consequently, it is advantageous if the toilet device can automatically detect urination.

Figure 25:
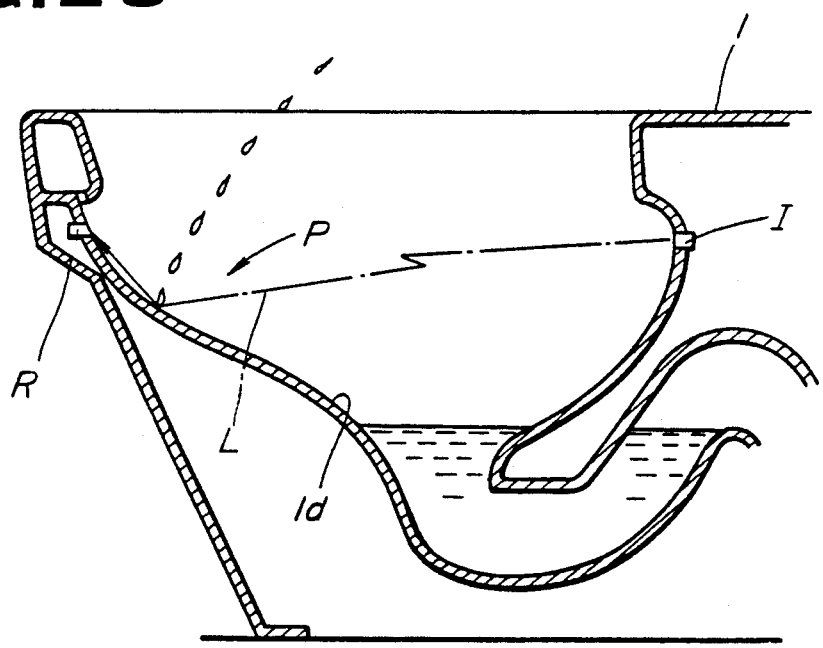
FIG. 25 is a cross-sectional view of a urination detecting mechanism which can be employed in the toilet device according to the present invention.

FIG. 25 shows a urination detecting mechanism which can be employed in the toilet device according to the present invention. With the urination detecting mechanism, the instructive sentence 119C and the switch 120C on the display panel 10 may be dispensed with, and hence the instructive information on the display panel 10 is simplified, with the result that the display panel 10 can be operated more easily.

In FIG. 25, a light-emitting element I is mounted on a rear portion of the bowl surface 1d of the toilet 1, and a light-detecting element R is mounted on a front portion of the bowl surface 1d. The light-emitting element I emits light L toward a region P where the urine impinges upon the bowl surface 1d, and the light-detecting element R detects light reflected from the region P.

Following the instructive sentences 119A, 119B on the display panel 10, the user opens the lid 404, sets a new urine test paper piece 6 in the holder 414, is seated on the seat 1b, and then urinates. Upon urination, urine droplets form surface irregularities in the region P, and light from the light-emitting element I is irregularly reflected by the surface irregularities. When the irregular reflection of light is detected by the light-detecting element R, the urination detecting mechanism actuates the lifting and lowering mechanism 400 in response to a detected signal from the light-detecting element R, thereby starting a urine analysis process. More specifically, the lower end of the urine test paper piece 6 is immersed in the urine reservoir 1e for a given period of time, and the lifting and lowering mechanism 400 is then reversed to lift the urine test paper piece 6 up to the position in front of the urine analyzing device 4, which measures the proportions of constituents of the urine sample based on the colors of the reagents impregnated with the urine sample. Thereafter, the urine test paper piece 6 with the analyzed urine sample is lowered to a position directly above the urine reservoir 1e by the lifting and lowering mechanism 400, and then the urine test paper piece 6 is discarded from the holder 414 into the urine reservoir 6.

With the above urination detecting mechanism, since urination can reliably be detected, a series of operations of the urine analyzing mechanism can automatically be started at suitable timing, and the user is allowed to operate the display panel more easily.

In case the urination detecting mechanism is simply incorporated in the toilet device according to the present invention, when a user wishes to have his urine analyzed, the urination detecting mechanism detects urination and automatically lowers a urine test paper piece 6 into the urine sample. After the urine test paper piece 6 has been immersed in the urine sample, it is lifted for a urine analysis by the urine analyzing device 4. Upon confirming that the urine test paper piece 6 has been lifted, the user may press the bowl washing switch 109A on the remote control panel 109 on the display panel 10 so that the toilet 1 will be washed by such a manual command. With the urination detecting mechanism employed, it is also possible to automatically lower the urine test paper piece 6, after being analyzed, toward the urine reservoir 1e with the lifting and lowering mechanism 400, so that the urine test paper piece 6 will drop into the urine reservoir 1e. Therefore, where the urination detecting mechanism is incorporated, or where the slider 413 is associated with the remover mechanism for discarding the used urine test paper piece 6 from the holder 414 without the urination detecting mechanism, if the user manually instructs the toilet device to wash the bowl surface 1d before the used urine test paper piece 6 is discarded, then the user may leave the toilet device, not knowing that the used urine test paper piece 6 is discarded into the urine reservoir 1e after the bowl surface 1d has been washed, so that the used urine test paper piece 6 may be left on the washed bowl surface 1d. When this happens, a next user of the toilet device may feel embarrassed, and the used urine test paper piece 6 in the urine reservoir 1e may present an obstacle to a next urine sampling operation. The toilet device according to the present invention may be combined with an automatic bowl washing mechanism which will solve the above problem. The automatic bowl washing mechanism will now be described with reference to FIGS. 26 through 28.

Figure 26:
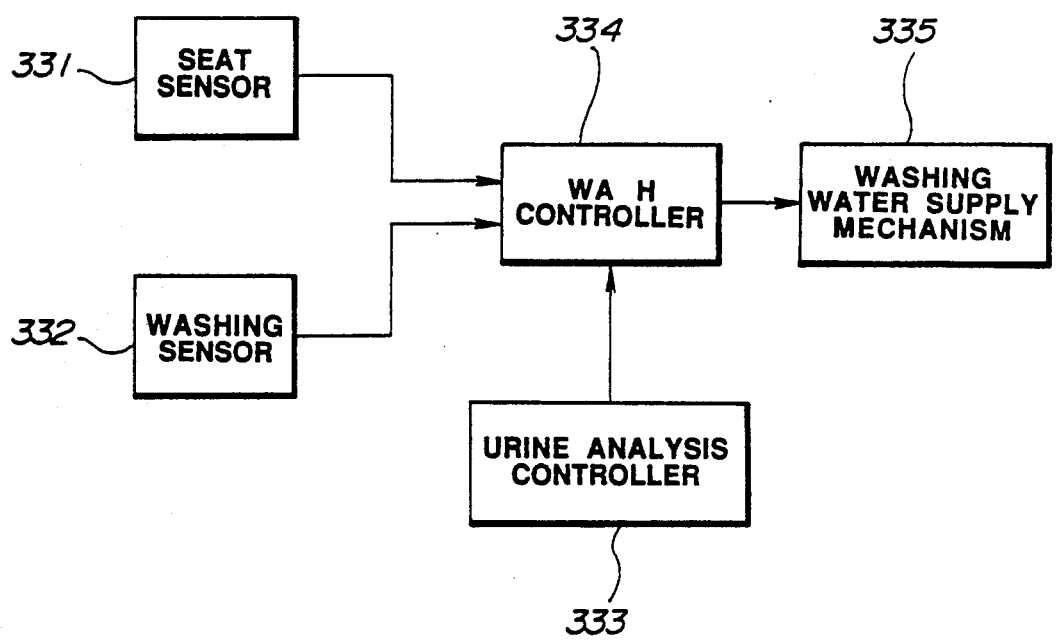
FIG. 26 is a block diagram of an automatic bowl washing mechanism that can be employed in the toilet device according to the present invention.

As shown in FIG. 26, the automatic bowl washing mechanism comprises a seat sensor 331 for detecting when the user is seated on the seat 1b, a washing sensor 332 for detecting when the bowl surface 1d is washed in response to a manual washing command from the user, a washing water supply mechanism 335 coupled to the water tank 3 for supplying washing water to the toilet 1, a urine analysis controller 333 for controlling the lifting and lowering mechanism 400 and the urine analyzing device 4, and a washing controller 334 for controlling the washing water supply mechanism 335 to supply washing water to the bowl 1d in response to detected signals from the seat sensor 331 and the washing sensor 332 and a discard signal from the urine analysis controller 333, indicating that the urine test paper piece 6 has been discarded into the urine reservoir 1e in the bowl 1d. The urine analysis controller 333 and the washing controller 334 may be implemented by a microcomputer, and disposed in the control box 7, for example.

Figure 27:
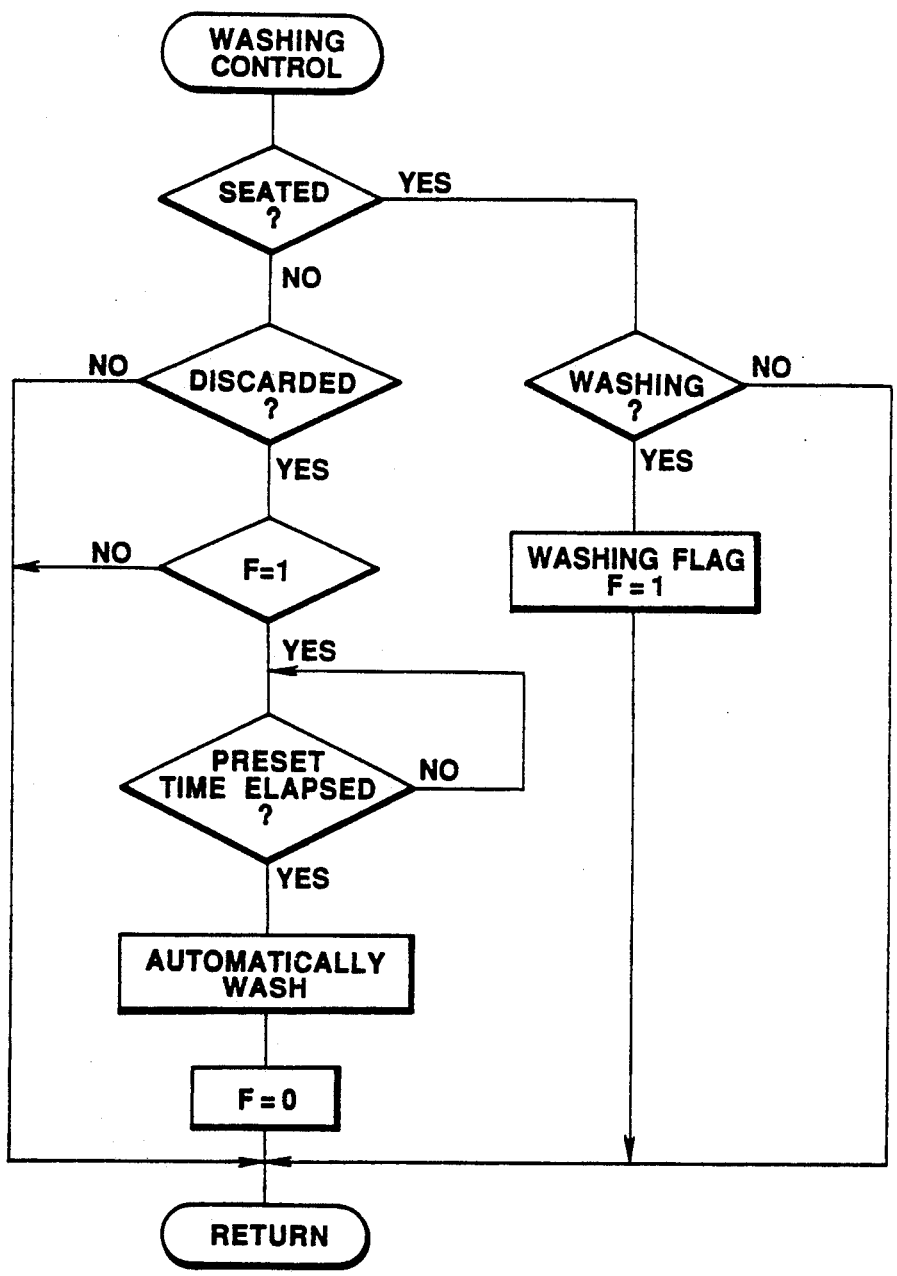
FIG. 27 is a flowchart of an operation sequence of the automatic bowl washing mechanism shown in FIG. 26.

Operation of the automatic bowl washing mechanism will be described with reference to the flowchart of FIG. 27.

The washing controller 334 determines whether the user is seated or not based on the seat signal from the seat sensor 331. If the user is seated, the washing controller 334 checks the washing signal from the washing sensor 332 to determine whether the bowl surface 1d of the toilet 1 is supplied with washing water, and sets a washing flag F to 1 if the bowl surface 1d is washed. If the seat signal from the seat sensor 331 indicates that the user is not seated, then the washing controller 334 checks whether the discard signal is delivered from the urine analysis controller 333 or not, thereby determining whether the urine test paper piece 6 is discarded into the urine reservoir 1e or not. If the urine test paper piece 6 is discarded into the urine reservoir 1e, the washing controller 334 checks whether the washing flag F is 1 or not, i.e., whether the toilet bowl 1d has already been washed or not. If the bowl 1d has already been washed, then the washing controller 334 controls the washing water supply mechanism 335 to supply washing water to the bowl 1d after elapse of a preset period of time, e.g., 1 minute, thus washing the bowl 1d. Then, the washing controller 334 resets the washing flag F to 0.

Figure 28:
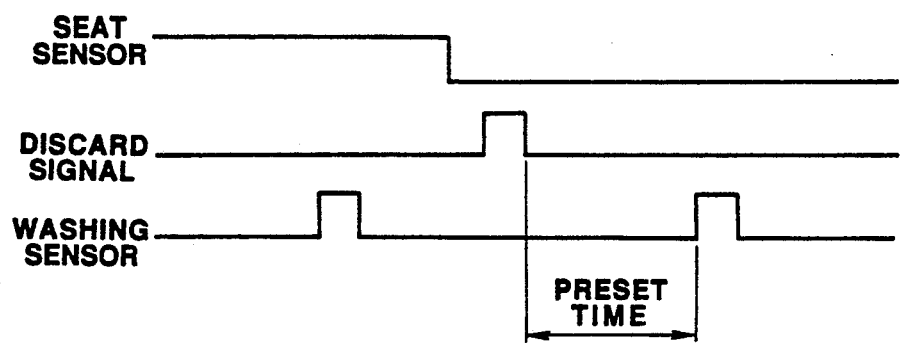
FIG. 28 is a timing chart of signals with respect to the automatic bowl washing mechanism shown in FIG. 26.

For example, as shown in FIG. 28, if the washing signal is delivered from the washing sensor 332 to detect that the bowl 1d is washed in response to a manual washing command from the user while the seating signal from the seat sensor 331 indicates that the user is seated, the bowl 1d is automatically washed upon elapse of the preset period of time after the discard signal is applied. Therefore, even if the toilet 1 is washed by the user before the urine test paper piece 6 is discarded, no used urine test paper piece 6 is left in the toilet 1.

With the automatic bowl washing mechanism thus used, if the toilet 1 is manually washed before the urine test paper piece 6 is discarded, the toilet 1 is automatically washed again. Accordingly, any used urine test paper piece 6 will not be left in the toilet 1, and any urine sampling operation is not obstructed and a next user of the toilet 1 is not embarrassed by the used urine test paper piece 6 which would otherwise be left in the urine reservoir 1e.

If the urination detecting mechanism and the automatic bowl washing mechanism are not incorporated in the toilet device according to the present invention, then the user may manually wash the toilet 1 (by pushing the toilet washing switch 109A on the remote control panel 109) without pushing the switch 120C on the display panel 10 after urination, or may manually wash the toilet 1 (by pushing the switch 109A) before the urine test paper piece 6 is lowered to pick up a urine sample by the lifting and lowering mechanism 400 even if the switch 120C is pushed.

The toilet device according to the present invention also has a local region washing device for moving the local region washer 5 shown in FIG. 1 into and out of the bowl 1d of the toilet 1. Even while the lifting and lowering mechanism 400 is being actuated to lower the urine test paper piece 6 held by the holder 414 toward the urine reservoir 1e, some user may wish to have his local body region washed and press a posterior washing switch 109B or a bidet washing switch 109c on the remote control panel 109.

When the local region washing device including the toilet washing function is operated, the urine sample in the urine reservoir 1e may be contaminated or flushed away, and the urine sample cannot be analyzed accurately.

To avoid the above trouble, the toilet device according to the present invention may have a mutual operation deterring mechanism for mutually deterring operation of the urine analyzing mechanism and the local region washing mechanism including the toilet washing function. The mutual operation deterring mechanism may be employed as an alternative to the urination detecting mechanism and the automatic bowl washing mechanism, but these mechanisms may be combined and incorporated in the toilet device according to the present invention. The mutual operation deterring mechanism will now be described below with reference to FIGS. 29 through 31.

FIG. 29 shows in block form the mutual operation deterring mechanism. As shown in FIG. 29, the mutual operation deterring mechanism includes a posterior washing instructing unit 711 for instructing posterior washing, a bidet washing instructing unit 712 for instructing bidet washing, and a bowl washing instructing unit 713 for instructing bowl washing. The mutual operation deterring mechanism also has a local region washing controller 714 for controlling a washing mechanism 715 based on instruction signals from the posterior washing instructing unit 711, the bidet washing instructing unit 712, and the bowl washing instructing unit 713, and ignores these instruction signals when a local region washing inhibition signal is supplied from a washing inhibition instructing unit 720, and applies an operation signal to a urine test or analysis inhibition instructing unit 716 while the toilet is being washed. The urine analysis inhibition instruction unit 716 applies a urine analysis inhibition signal to a urine analysis controller 718 while an operation signal is being supplied from the local region washing controller 714.

A urine analysis instructing unit 717 instructs a urine analysis. The urine analysis controller 718 controls a urine analyzing mechanism 719 to effect the urine analysis based on a analysis instruction signal from the urine analysis instructing unit 717, and ignores the urine analysis instruction signal while the urine analysis inhibition signal is being supplied from the urine analysis inhibition instructing unit 716. The controller 718 also applies an operation signal to the washing inhibition instructing unit 720 while the urine analysis is being carried out.

Operation of the mutual operation deterring mechanism thus constructed will be described with reference to FIGS. 30 and 31.

Figure 30:
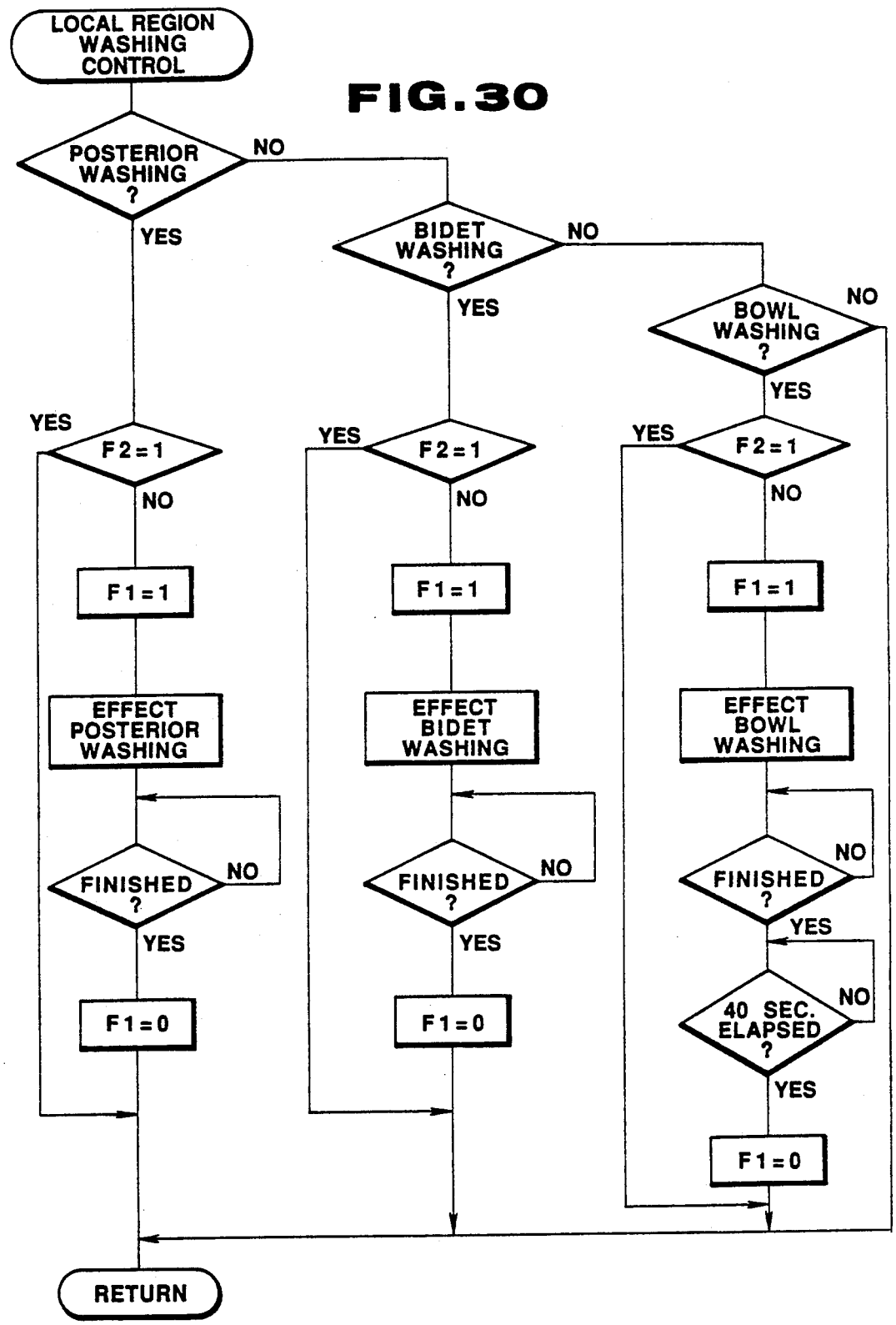
FIG. 30 is a flowchart of an operation sequence of a local region washing controller in the mutual operation deterring mechanism shown in FIG. 29.

As shown in FIG. 30, when a posterior washing instruction is given, the local region washing controller 714 determines whether a washing inhibition flag F2 is 1 or not, which flag is set to 1 when a washing inhibition signal is supplied from the washing inhibition instructing unit 720. If the washing inhibition flag F2 is set to 1, then the posterior washing instruction is ignored and no posterior washing is effected. If the washing inhibition flag F2 is not set to 1 when the posterior washing instruction is given, then the local region washing controller 714 applies an operation signal to the urine analysis inhibition instructing unit 716, which then produces a urine analysis inhibition signal. After the local region washing controller 714 sets a urine analysis inhibition flag F1 to 1, it controls the washing mechanism 715 to effect posterior washing, after which the local region washing controller 714 resets the urine analysis inhibition flag F1 to 0.

When a bidet washing instruction is given, it is ignored and bidet washing is not effected if the washing inhibition flag F2 is set to 1. If the washing inhibition flag F2 is not set to 1, the urine analysis inhibition flag F1 is set to 1, and thereafter the washing mechanism 715 is controlled to effect bidet washing. After the bidet washing is finished, the urine analysis inhibition flag F1 is reset to 0.

When a bowl washing instruction is given, it is ignored and not bowl washing is effected if the washing inhibition flag F2 is set to 1. If the washing inhibition flag F2 is not set to 1, the urine analysis inhibition flag F1 is set to 1, and thereafter the washing mechanism 715 is controlled to effect bowl washing. After the bowl washing is finished, the urine analysis inhibition flag F1 is reset to 0 after elapse of a preset period of time, e.g., 40 seconds. The preset period of time is necessary since a large amount of water is supplied to wash the bowl and it takes a certain period of time to supply the entire washing water.

Figure 31:
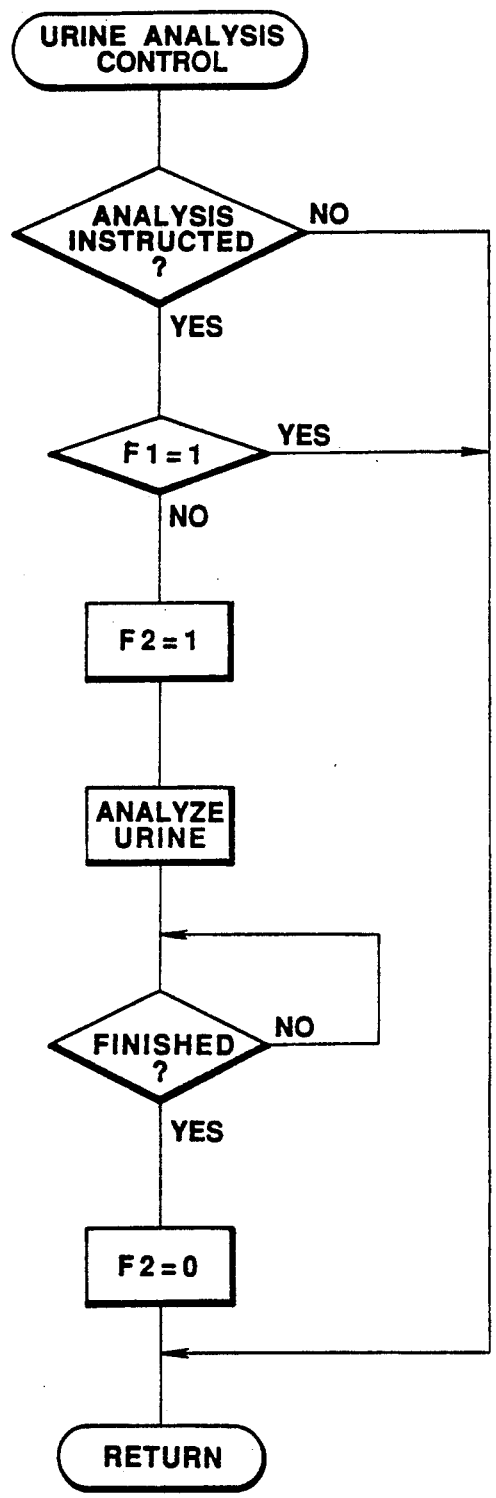
FIG. 31 is a flowchart of an operation sequence of a urine analysis controller in the mutual operation deterring mechanism shown in FIG. 29.

As shown in FIG. 31, when a urine analysis instruction is given, the urine analysis controller 718 determines whether the urine analysis inhibition flag F1 is set to 1. If the urine analysis inhibition flag F1 is set to 1, the urine analysis controller 718 ignores the urine analysis instruction. If the urine analysis inhibition flag F1 is not set to 1, the urine analysis controller 718 applies an operation signal to the washing inhibition instructing unit 720, which produces a washing inhibition signal. After the urine analysis controller 718 sets the washing inhibition flag F2 to 1, it controls the urine analyzing mechanism 719 to effect a urine analysis, and resets the washing inhibition flag F2 to 0 after the urine analysis is finished.

As described above, during the washing process, any urine analysis is inhibited, and during the urine analysis, any washing process is inhibited. Accordingly, the urine analysis and the washing process are deterred at respective timings, and hence can smoothly be effected one at a time. The above mutual deterring function is particularly effective to prevent the lifting and lowering mechanism 400 from being damaged or the urine sample in the urine reservoir 1e from being contaminated before being analyzed.

The toilet device according to the present invention can examine urine constituents and blood pressures, as described above. Furthermore, the toilet device may also have a function to measure the body weight of the user since the entire weight of the user is paced almost entirely on the toilet 1, with the display panel 10 being partly modified for the display of the measured weight. A body weight measuring mechanism for the toilet device according to the present invention will now be described with reference to FIGS. 32 through 40.

Figure 32:
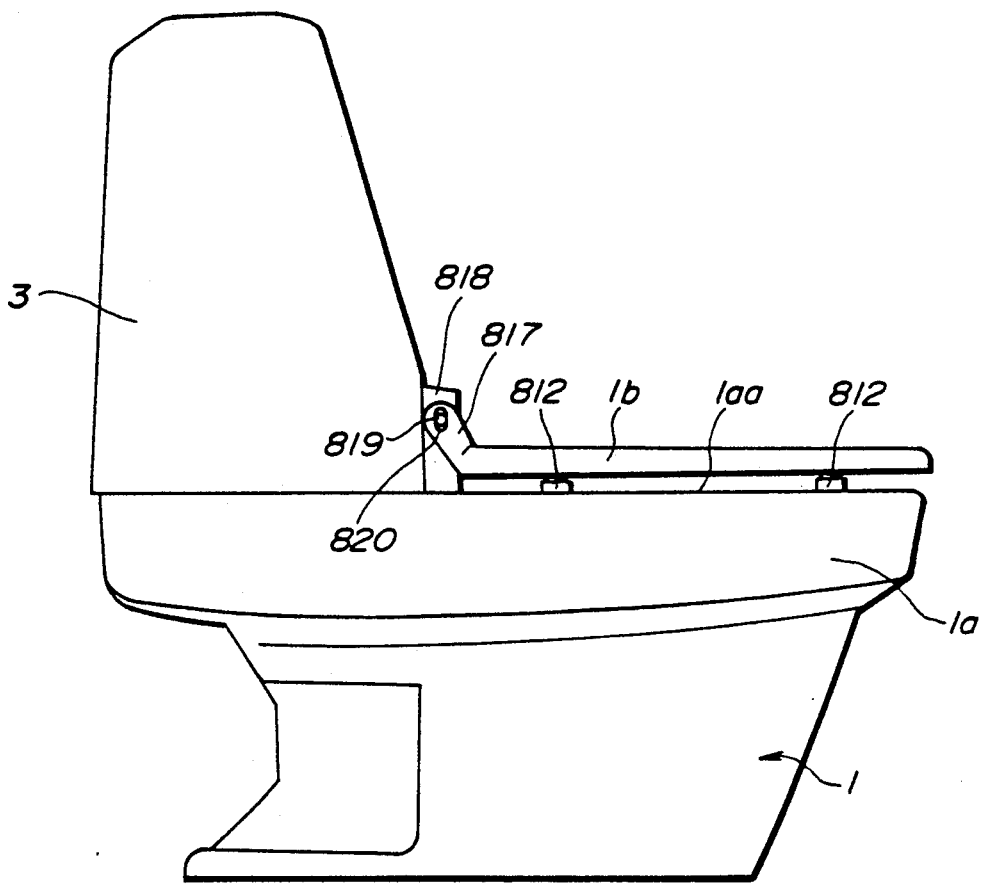
FIG. 32 is a side elevational view of a body weight measuring mechanism that can be employed in the toilet device according to the present invention.
Figure 33:
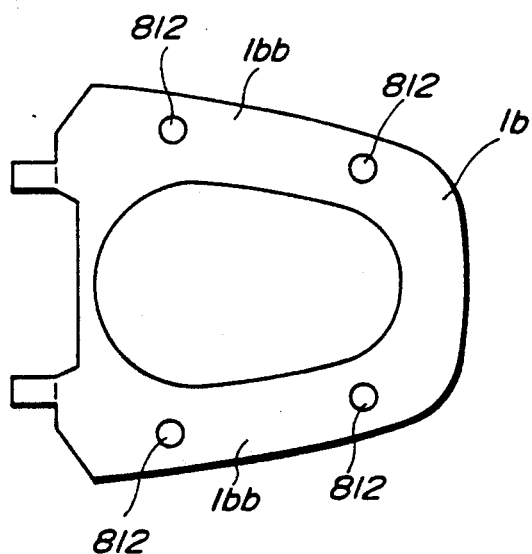
FIG. 33 is a bottom view of a seat of the body weight measuring mechanism shown in FIG. 32.
Figure 34:
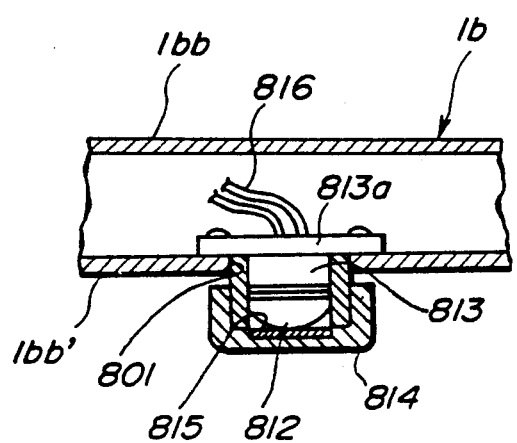
FIG. 34 is a fragmentary cross-sectional view of a body weight detector fitted in the seat.

FIG. 32 shows in side elevation a modification of the toilet 1 shown in FIG. 1. The toilet 1 has a rim 1a on its upper portion, and a seat 1b positioned on the rim 1a. The seat 1b is of a loop shape having a certain width, as shown in FIG. 33, the seat 1b being substantially complementary to an upper surface 1aa of the rim 1a. The seat 1b has left and right side members 1bb with body weight detectors 812 mounted on the lower surfaces thereof, the body weight detectors 812 being spaced in the longitudinal direction of the seat 1b. Each of the body weight detectors 812 comprises a semiconductor pressure sensor, for example. As shown in FIG. 34, the seat 34 is of a hollow box-like structure, and has a plurality of attachment holes 801 defined in a bottom plate 1bb' thereof. A semiconductor pressure sensor unit 813 is fitted in each of the attachment holes 801. The semiconductor pressure sensor unit 813 has a base 813a fixed to a peripheral edge of the attachment hole 801, and projects downwardly below the bottom plate 1bb'. The projecting unit 813 is covered with a cushion 814 which supports a protective plate 815 of iron, for example, that abuts against the bottom of the unit 813. The unit 813 produces an electric signal indicative of the body weight of the user seated on the seat 1b, and the electric signal is supplied to the display panel 10 over wires 816. The body weight calculated from the electric signal is displayed on the display panel 10. There are four body weight detectors 812 located in front left, front right, rear left, and rear right corners of the seat 1b, and the signals from these body weight detectors 812 are corrected to produce an accurate body weight value. However, two body weight detectors may be mounted respectively on the left and right side members of the seat 1b and a single body weight detector may be mounted on a front side member of the seat 1b.

Each of the body weight detectors 812 may be a load cell or any of other known pressure sensors.

Figure 35:
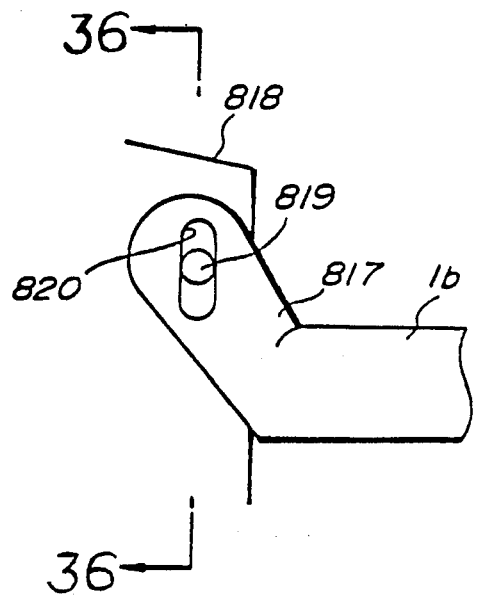
FIG. 35 is a fragmentary side elevational view of a pivot structure by which the seat of the toilet shown in FIG. 32 and a water tank are pivotally coupled to each other.
Figure 36:
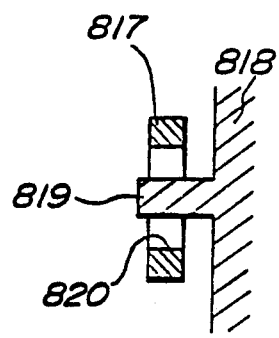
FIG. 36 is a cross-sectional view taken along line 36—36 of FIG. 35.

The seat 1b may be hinged to the water tank 3 as follows: The seat 1b has two attachment stays 817 on left and right portions of the rear edge thereof, the stays 817 being inclined rearwardly and upwardly. The water tank 3 has attachment bases 818 on opposite sides of a front lower portion thereof. As shown in FIGS. 35 and 36, the attachment bases 818 have respective shafts 819 projecting horizontally outwardly. The attachment stays 817 of the seat 1b have vertical oblong holes 820, respectively, which have a width large enough to allow the shafts 819 to be fitted therein The shafts 819 fitted in the respective oblong holes 820 are only vertically slidable therein.

When the user seated on the seat 1b lifts his feet off the floor, the entire body weight is applied to the seat 1b. Since the seat 1b is not hinged to the water tank 3 by a simple hinged construction, but is allowed to move vertically by the oblong holes 820, i.e. in the direction in which the body weight is applied, the seat 1b is loosely hinged to the water tank 3. Therefore, the body weight detectors 812 are not subject to tensile forces from the hinged portion of the seat 1b, but undergo only vertical forces as the body weight is applied vertically to the seat 1b that is freely vertically movable. Since no horizontal forces in the longitudinal direction of the seat 1b are applied to the body weight detectors 312, the body weight of the user seated on the seat 1b can accurately be measured.

Figure 37:
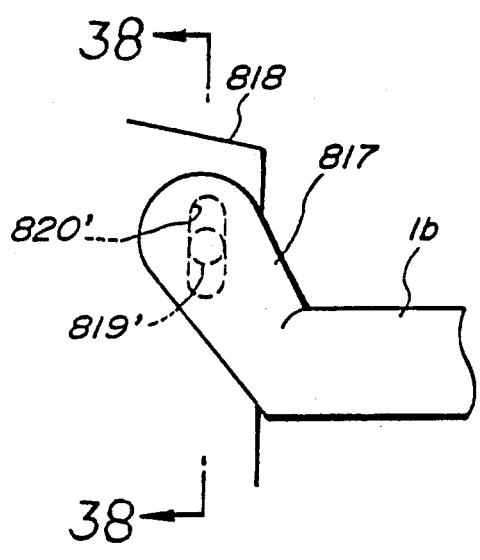
FIG. 37 is a fragmentary side elevational view of a modification of the pivot structure shown in FIG. 35.
Figure 38:
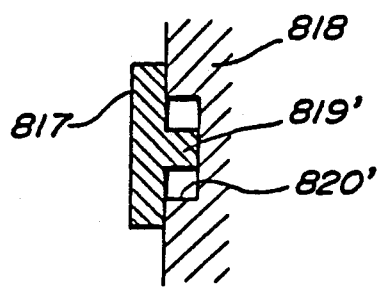
FIG. 38 is a cross-sectional view taken along line 38—38 of FIG. 37.

FIGS. 37 and 38 show another hinged structure. According to the arrangement shown in FIGS. 37 and 38, shafts 819' project from inner sides of attachment stays 817 on the seat 1b, and attachment bases 818 on the water tank 3 have vertical oblong holes 820' in which the respective shafts 819' are fitted.

Figure 39:
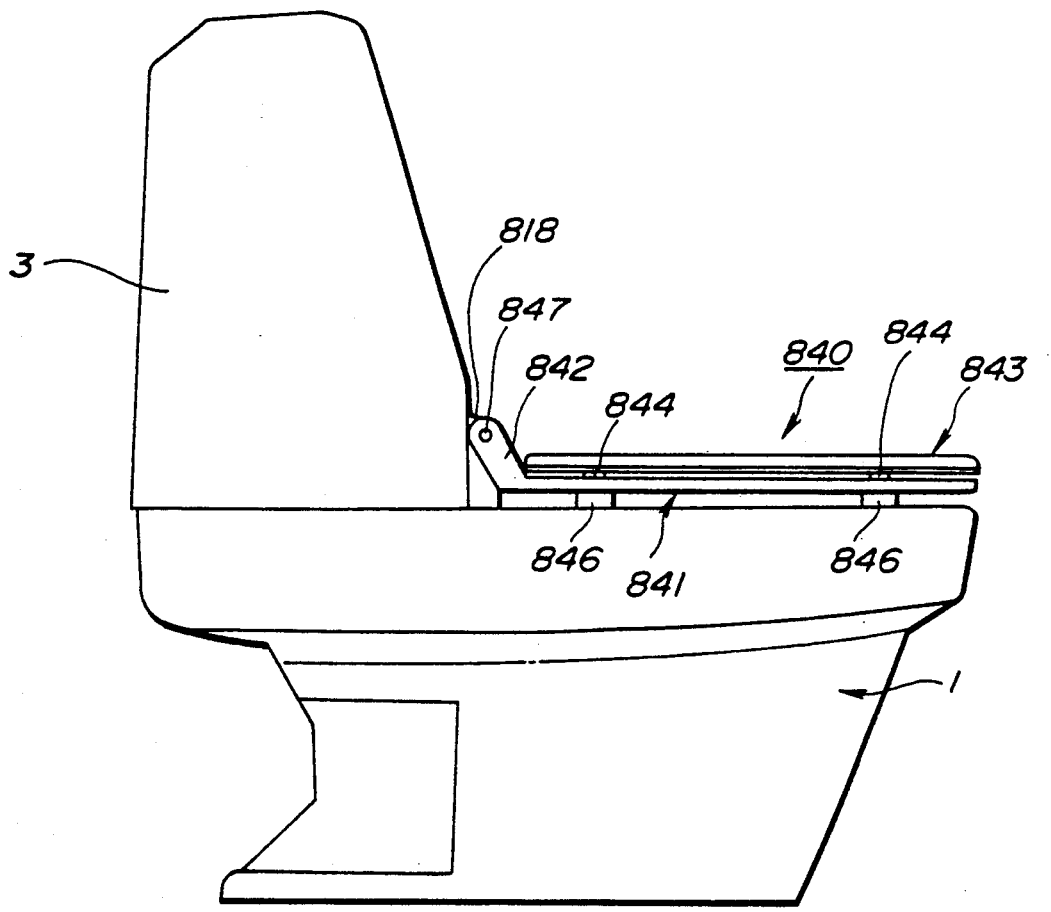
FIG. 39 is a side elevational view of a body weight measuring mechanism according to a modification.
Figure 40:
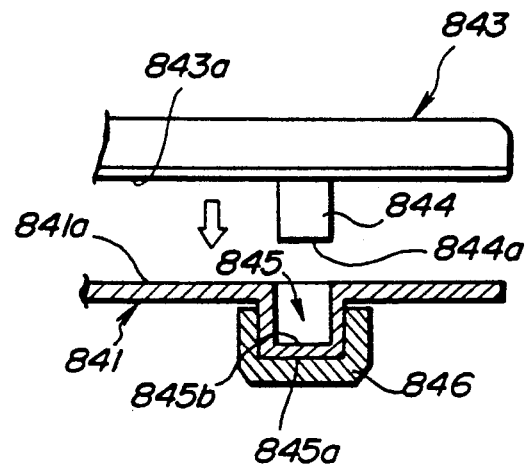
FIG. 40 is a fragmentary cross-sectional view of a seat including a body weight detector in the body weight measuring mechanism shown in FIG. 39.

FIGS. 39 and 40 show another body weight measuring mechanism.

A seat 840 is mounted on an upper surface 1aa of the rim 1a of the toilet 1. The seat 840 comprises lower first and upper second seat members 841, 843. The lower first seat member 841 has attachment stays 842 on left and right portions of the rear edge thereof, the attachment stays 842 being hinged to bases 818 on the water tank 3 by respective shafts 847. The first seat member 841 is therefore vertically angularly movable about the shafts 847. The second upper seat member 843 is placed on the first seat member 841, and serves as an actual seat on which the user will be seated.

The second seat member 843 supports body weight detectors 844 such as semiconductor pressure sensors, for example, projecting from a lower surface 843a thereof. The first seat member 841 has recesses 845 defined therein for receiving the respective body weight detectors 844 therein. Each of the recesses 845 is formed by projecting the plate of the first seat member 841 downwardly. A cushion 846 is mounted on an outer bottom surface 845a of the recess 845. The depth of the recess 845 is smaller than the distance by which the body weight detector 844 projects downwardly from the second seat member 843. Therefore, when lower ends 844a of the body weight detectors 844 contact inner bottom surfaces 845b of the recesses 845, respectively, there is left a sufficient gap between the upper surface 841a of the first seat member 841 and the lower surface 843a of the second seat member 843. The extent by which the body weight detectors 844 are fitted in the respective recesses 845 is such that when the seat 840 is erected vertically with the second seat member 843 placed on the first seat member 841, the first and second seat members 841, 843 will not separate easily from each other.

With the body weight measuring mechanism shown in FIGS. 39 and 40, the seat 840 is composed of upper and lower seat members. Since the lower seat member is hinged to the water tank and the upper seat member, on which the body weight of the user acts, is held only in fitting engagement with the lower seat member through the body weight detectors, only the body weight is applied to the body weight detectors 844, but no tensile forces are applied from the hinged portion of the seat to the body weight detectors 844. As only the downward body weight acts on the body weight detectors 844, the body weight detectors 844 can measure the body weight highly accurately.

In the toilet device according to the present invention, the urine test paper piece 6 is held by the holder 414, lowered into the urine reservoir 1e on the bowl surface 1d by the lifting and lowering mechanism 400, immersed in the urine sample in the urine reservoir 1e, and thereafter lifted into the position in front of the urine analyzing device 4. The urine sample itself can develop colors depending on the proportions of urine constituents when reagents are dropped directly into the urine sample. Such a urine analyzing arrangement, which does not employ any urine test paper, may be incorporated in the toilet device according to the present invention. The toilet device with such a direct urine analyzing system will now be described with reference to FIGS. 41 through 43.

Figure 41:
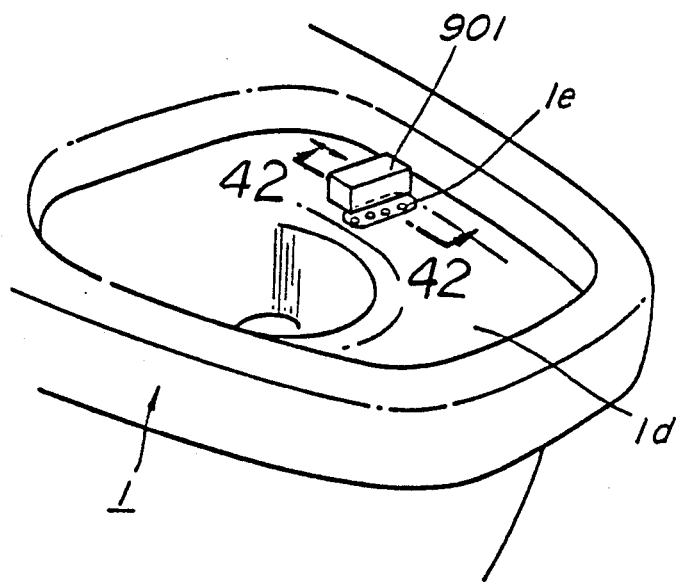
FIG. 41 is a perspective view of a toilet bowl incorporating a modified urine analyzing arrangement.
Figure 42:
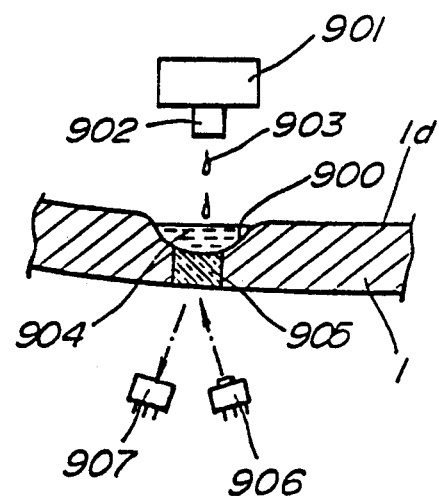
FIG. 42 is a fragmentary cross-sectional view taken along line 42—42 of FIG. 41.

As shown in FIG. 41, a urine reservoir 1e is composed of a transverse array of recesses 900 each serving as an independent urine reservoir for storing a urine sample upon urination. The number of recesses 900 is the same as the number of urine constituents to be measured. Therefore, when glucose, albumin, urobilinogen, and occult, for example, are to be measured, the urine reservoir 1e has four recesses 900. As shown in FIG. 42, a transparent body 905 of glass, for example, is fitted in the bottom of each of the recesses 900, and a reagent dropping unit 901 is positioned above the urine reservoir 1e. The reagent dropping unit 901 drops reagents 903 into urine samples in the recesses 900 through respective nozzles 902 extending downwardly from the reagent dropping unit 901. When the reagents 903 are added, the urine samples develop different colors depending on the constituents of the urine samples. The number of nozzles 902 of the reagent dropping unit 901 is therefore the same as the number of urine constituents to be measured, so that different reagents can be dropped through the nozzles 902, respectively, into the recesses 900. A light-emitting element 906 and a light-detecting element 907 are disposed below the transparent body 905 beneath each of the recesses 900.

For a urine analysis, a portion of urine voided by the user is uniformly received by the recesses 900, and the reagent dropping unit 901 is positioned directly above the recesses 900, after which respective reagents are dropped into the recesses 900. Light emitted from the light-emitting element 906 is reflected by the urine sample and detected by the light-detecting element 907. Based on the difference between the intensity of light reflected from the urine samples before the urine samples develop colors an the intensity of light reflected from (o transmitted through) the urine samples after the urine samples develop colors, the proportions of the constituents of the urine samples are calculated for urine analysis.

After dropping the reagents, the reagent dropping unit 901 should be retracted into a portion of the toilet 1. Therefore, the reagent dropping unit 901 is moved over the urine reservoir 1e only when a urine analysis is to be effected. The lifting and lowering mechanism 400 may be partly modified to construct the slider 413, rather than the holder 414, to hold the reagent dropping unit 901.

Figure 43:
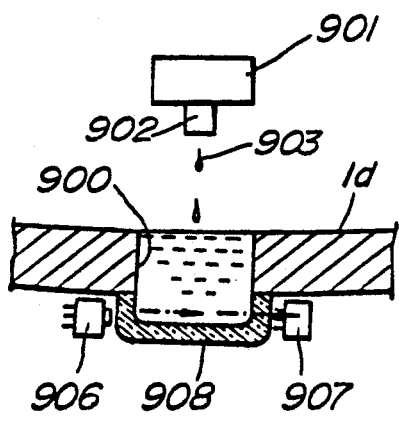
FIG. 43 is a fragmentary cross-sectional view of a urine reservoir according to a modification of the toilet bowl shown in FIG. 42.

FIG. 43 shows a modification of the arrangement shown in FIG. 42. A hole defined in the bowl surface 1d is closed by a transparent cap 908, thus serving as a urine reservoir, and a light emitting element 906 and a light-detecting element 907 are disposed on opposite sides of the transparent cap 908.

Although there have been described what are at present considered to be the preferred embodiments of the pre sent invention, it will be understood that the invention may be embodied in other specific forms without departing from the essential characteristics thereof. The present embodiments are therefore to be considered in all aspects as illustrative, and not restrictive. The scope of the invention is indicated by the appended claims rather than by the foregoing description.

What is claimed is:

1. A toilet device comprising:
   a toilet having a bowl surface and a urine reservoir composite with said bowl surface and isolated therein for holding a urine sample;
   a housing having at least a water tank disposed rearwardly and upwardly of said toilet, said housing having an outlet opening in a bottom thereof;
   a slider mounted within said housing for holding a urine test paper piece, said slider being movable from within said housing toward said urine reservoir to immerse the urine test paper piece in the urine sample in said urine reservoir;
   a urine analyzing device disposed in said housing, for analyzing constituents of the urine sample based on said urine test paper piece which has been immersed in the urine sample;
   a lifting and lowering mechanism disposed in said housing for reciprocally lifting and lowering said slider through said outlet opening along a substantially vertical inclined path between said urine analyzing device and said urine reservoir; and
   a display panel associated with said toilet device for controlling said lifting and lowering mechanism and said urine analyzing device and for displaying results of a urine analysis effected by said urine analyzing device.

2. A toilet device according to claim 1, wherein said lifting and lowering mechanism comprises means for lowering said slider to discard the analyzed urine test paper piece into said urine reservoir after a urine analysis effected by said urine analyzing device, said toilet device further comprising a seat sensor for detecting when the user of the toilet is seated on a seat of said toilet and producing a seat signal indicative of the seating of the user, a washing sensor for detecting when said bowl surface is washed in response to a manual washing command from the user and producing a washing signal indicative of the washing of the bowl surface, washing water supply means connected to said water tank for supplying washing water to said bowl surface, urine analysis control means connected to said urine analyzing device and said lifting and lowering mechanism, for producing a discard signal indicating that the urine test paper piece after the urine analysis is discarded into said urine reservoir, and washing control means responsive to said seat signal, said washing signal, and said discard signal for actuating said washing water supply means to supply washing water to said bowl surface if the washing signal is produced while said seat signal is being produced and if said discard signal is produced after said seat signal is removed.

3. A toilet device according to claim 1, further including cover means for substantially covering said slider.

4. A toilet device according to claim 3, wherein said cover means is extensible and contractable as said slider is lifted and lowered through said outlet opening.

5. A toilet device according to claim 3, wherein said cover means comprises a cover member and washing means for washing a downwardly extending outer surface of the cover member.

6. A toilet device according to claim 1, wherein said lifting and lowering mechanism includes a rail for moving said slider therealong from said outlet opening toward said urine reservoir, said rail extending at least from said urine analyzing device to said outlet opening.

7. A toilet device according to claim 6, further including a shutter mechanism for opening and closing said outlet opening in response to lifted and lowered movement of said slider.

8. A toilet device according to claim 6, further including a base plate fixed to said toilet and supporting a plurality of vertical bolts, said lifting and lowering mechanism comprising a frame disposed in said housing and supporting said rail, said frame having a bottom plate mounted on said base plate, said bottom plate having bolt insertion holes aligned with said bolts, respectively, and having a size larger than the diameter of said bolts, said bolts being inserted through said bolt insertion holes, respectively, said bottom plate being adjustably fastened above said base plate by nuts threaded over said bolts above and below the bottom plate, whereby said rail can be positionally adjusted with respect to the location of said urine reservoir.

9. A toilet device according to claim 1, wherein said urine test paper piece has on a surface thereof reagent regions for reacting with the urine sample, said slider having a holder mounted on a lower end thereof, for holding the urine test paper piece which is inserted into said box through an openable and closable lid on said box when said slider is positioned above said urine analyzing device by said lifting and lowering mechanism.

10. A toilet device according to claim 9, wherein said holder has a lever mechanism which can be brought into different angular positions when engaged by the face and back, respectively, of the urine test paper piece held by said holder.

11. A toilet device according to claim 10, wherein said urine test paper piece is laterally asymmetric in shape, said lever mechanism comprising two levers which can engage lateral sides, respectively, of said urine test paper piece.

12. A toilet device according to claim 9, wherein said display panel includes an instructive panel area for controlling said lifting and lowering mechanism and said urine analyzing device, said instructive panel area including a first instructive message for instructing the user of the toilet to insert a new urine test paper piece into said holder, a second instructive message for instructing the user to urinate, a third instructive message for instructing said lifting and lowering mechanism and said urine analyzing device to start a urine analysis after urination, symbol indications associated with said first and second instructive messages, respectively, and giving visual images of the first and second instructive messages, and a switch associated with said third instructive message for initiating operation of said lifting and lowering mechanism and said urine analyzing device.

13. A toilet device according to claim 12, wherein said display panel also has a display panel area adjacent to said instructive panel area and light-emitting means for applying light to a reverse side of said display panel area, said display panel area bearing a plurality of marks indicative of steps of health data and substantial quantitative values corresponding to and associated with said marks, respectively, said light-emitting means being energizable to apply light to one of said marks and a corresponding one of said quantitative values which corresponds to the result of the urine analysis which is effected according to said third instructive message.

14. A toilet device according to claim 13, wherein said steps of health data in said display panel area are differently colored.

15. A toilet device according to claim 9, further including light-emitting means for applying a light to a region of said bowl surface which is impinged by urine voided by the user of the toilet, light-detecting means for detecting light reflected from said region of the bow surface, and a urination detecting mechanism for detecting urination of the user based on irregularly reflected light from surface irregularities produced on said region of the bowl surface due to the urination of the user.

16. A toilet device according to claim 15, wherein said urination detecting mechanism comprises means for actuating said lifting and lowering mechanism and said urine analyzing device after detecting the urination, thereby effecting a urine analysis.

17. A toilet device according to claim 16, wherein said urination detecting mechanism comprises means for actuating said lifting and lowering mechanism to lower said slider after the urine analysis, and causing said holder to discard the analyzed urine test paper piece into said urine reservoir.

18. A toilet device according to claim 1, further including blood pressure measuring means for measuring at least the blood pressure of the user of the toilet and displaying the measured blood pressure on said display panel.

19. A toilet device according to claim 18, wherein said blood pressure measuring means comprises a hand rest having a cuff for receiving a finger of the user seated on said toilet, and a control box disposed alongside of said toilet, for measuring the blood pressure of the user through said cuff, said hand rest being positioned on an upper surface of said control box, said cuff being angularly movable with respect to said hand rest.

20. A toilet device according to claim 19, wherein said control box has a cylinder unit for lifting said cuff, which receives the finger of the user seated on said toilet, to the same height as the heart of the user.

21. A toilet device according to claim 19, wherein said blood pressure measuring means comprises means for correcting the blood pressure directly measured through said cuff with a height difference between said cuff and the heart of the user, and for displaying the corrected blood pressure on said display panel.

22. A toilet device according to claim 19, further including a bathroom in which said toilet is installed, said bathroom having a side wall, said display panel being mounted on said side wall and having an optical data transmitter and receiver unit for transmitting and receiving data relative to control and display functions of said display panel, said control box having an optical data transmitter and receiver unit for transmitting and receiving data relative to said lifting and lowering mechanism, said urine analyzing device, and said blood pressure measuring means, said display panel and said control box being connected to each other by an optical communication link through said transmitter and receiver units.

23. A toilet device according to claim 1, further including a mutual operation deterring mechanism which comprises:
a washing mechanism for washing said bowl surface, said washing mechanism including a local region washer movable into and out of a bowl of said toilet, for washing a local body region of the user of the toilet;
washing instructing means for producing a washing instruction signal;
urine analysis instructing means for producing a urine analysis instruction signal;
washing control means responsive to the washing instruction signal from said washing instructing means, for producing an operation signal and actuating said washing mechanism to effect a washing process;
urine analysis control means responsive to the urine analysis instruction signal from said urine analysis instructing means, for producing an operation signal and actuating said lifting and lowering mechanism and said urine analyzing device to analyze the urine sample;
washing inhibition instructing means responsive to the operation signal from said urine analysis control means, for producing a washing inhibition signal to enable said washing control means to inhibit washing processes effected by said washing mechanism while said operation signal from said urine analysis control means is being applied; and
urine analysis inhibition instructing means responsive to the operation signal from said washing control means, for producing a urine analysis inhibition signal to enable said urine analysis control means to inhibit a urine analysis effected by said lifting and lowering mechanism and said urine analyzing device while said operation signal from said washing control means is being applied.

24. A toilet device according to claim 1, further including a seat loosely hinged to said housing and swingably movable onto and away from a rim of said toilet, and a body weight detector disposed between said seat and said rim.

25. A toilet device according to claim 24, wherein said body weight detector is embedded in a lower surface of said seat, said seat being loosely hinged to said housing by a member having a vertical oblong hole and a shaft engaging in said oblong hole.

26. A toilet device according to claim 1, further including a body weight detecting mechanism comprising:
a first seat member hinged to said housing and swingably movable onto and away from a rim of said toilet;
a second seat member mounted on said first seat member; and
a body weight detector disposed between said first and second seat members and holding said first and second seat members in engagement with each other.

27. A toilet device according to claim 26, wherein said body weight detector projects from a lower surface of said second seat member, and said first seat member has in an upper surface thereof a recess in which said projecting body weight detector is fitted.

28. A toilet device comprising:
a toilet having a bowl surface and a urine reservoir composite with said bowl surface and isolated therein for holding a urine sample, said urine reservoir having a transparent body;
slider means connected to said toilet and movable toward said urine reservoir, for effecting a process related to a urine analysis, using the urine sample in said urine reservoir, said slider means including reagent dropping means for dropping reagents, which cause the urine sample to develop different colors depending on proportions of constituents of the urine sample, into said urine reservoir;
a urine analyzing device connected to said toilet for effecting the urine analysis of the urine sample in relation to said process, said urine analyzing device including a light-emitting element and a light-detecting element which are disposed below said transparent body;
sliding means connected to said toilet for reciprocally moving said slider means toward said urine reservoir; and
display means associated with said toilet device for controlling said sliding means and said urine analyzing device and for displaying results of the urine analysis effected by said urine analyzing device.

29. A toilet device according to claim 28, wherein said urine reservoir has as many recesses as the number of the constituents of the urine sample which are to be analyzed, and said reagent dropping means having as many dropping nozzles as the number of the constituents, for dropping respective different reagents into said recesses, respectively.

30. A toilet device comprising:
a toilet having a bowl surface and a urine reservoir composite with said bowl surface and isolated therein for holding a urine sample;

a housing having at least a water tank disposed rearwardly and upwardly of said toilet, said housing having an outlet opening in a bottom thereof;

a slider mounted within said housing for holding a urine test paper piece, said slider being movable from within said housing toward said urine reservoir to immerse the urine test paper piece in the urine sample in said urine reservoir;

a urine analyzing device disposed in said housing for analyzing constituents of the urine sample based on said urine test paper piece which has been immersed in the urine sample; and a lifting and lowering mechanism disposed in said housing for reciprocally lifting and lowering said slider through said outlet opening along a substantially vertical inclined path between said urine analyzing device and said urine reservoir.

31. A toilet device according to claim 30, wherein said lifting and lowering mechanism includes a guide rail for moving said slider therealong from said outlet opening toward said urine reservoir, said rail extending at least from said urine analyzing device to said outlet opening.

32. A toilet device according to claim 30, further including a display panel associated with said toilet device for controlling said lifting and lowering mechanism and said urine analyzing device and for displaying results of a urine analysis effected by said urine analyzing device.

33. A toilet device according to claim 32, further including a blood pressure measuring means and a bathroom in which said toilet is installed, said bathroom having a side wall, said display panel being mounted on said side wall and having an optical data transmitter and receiver unit for transmitting and receiving data relative to control and display functions of said display panel, said housing having an optical data transmitter and receiver unit for transmitting and receiving data relative to said lifting and lowering mechanism, said urine analyzing device. and said blood pressure measuring means, said display panel and said housing being connected to each other by an optical communication link through said transmitter and receiver units.

34. A toilet device comprising:

a toilet having a bowl surface and a urine reservoir composite with said bowl surface and isolated therein for holding a urine sample;

a housing having at least a water tank disposed rearwardly and upwardly of said toilet, said housing having an outlet opening in a bottom thereof;

slider means disposed in said housing and movable from said housing toward said urine reservoir, for effecting a process related to a urine analysis, using the urine sample in said urine reservoir, said slider means including holder means for holding a urine test paper piece which develops colors depending on constituents of the urine sample;

a urine analyzing device disposed in said housing for effecting the urine analysis of the urine sample in relation to said process, said urine analyzing means including means for optically analyzing the urine test paper piece held by said holder means;

sliding means disposed in said housing for reciprocally moving said slider means from said urine analyzing device toward said urine reservoir so as to lift and lower said slider means along a substantially vertical inclined path between said urine analyzing device in said housing and said reservoir; and means and said urine analyzing device and for displaying results of the urine analysis effected by said urine analyzing device.

35. A toilet device according to claim 34, wherein said holder means comprises means for dropping the urine test paper piece with the urine sample analyzed into said urine reservoir, after said holder means and said slider means are lowered toward said urine reservoir by said lifting and lowering mechanism.

* * * * *

UNITED STATES PATENT AND TRADEMARK OFFICE
CERTIFICATE OF CORRECTION

PATENT NO. : 5,111,539
DATED : May 12, 1992
INVENTOR(S) : Yoshiki Hiruta; Naoki Tsukamura; Yoshinobu Uchimura; Toshifumi Shigematsu; Hironori Yamasaki; and Toshio Yamaguchi It is certified that error appears in the above-identified patent and that said Letters Patent is hereby corrected as shown below:

Column 2, line 12, change "pane" to -- panel --.
Column 4, line 13, change "ca" to -- can --.
Column 6, line 17, change "sot" to -- slot --;
        line 65, change "S2" to -- $S_2$ --.
Column 8, line 25, change "roamer" to -- roller --.
Column 9, line 58, change "from" to -- fro --.
Column 13, line 40, change "printed circuit" to -- printed-circuit --.
Column 18, line 38, change "a" to -- an --.
Column 19, line 7, delete "not";
        line 7, change "is" to -- is not --;
        line 46, change "paced" to -- placed --.
Column 20, line 32, change "therein The" to -- therein. The --.
Column 22, line 17, change "an" to -- and --;
        line 18, change "(o" to -- (or --;
        line 33, change "light emitting" to -- light-emitting --;
        line 38, change "pre sent" to -- present --.

UNITED STATES PATENT AND TRADEMARK OFFICE
CERTIFICATE OF CORRECTION

PATENT NO. : 5,111,539

DATED : May 12, 1992

INVENTOR(S) : Yoshiki Hiruta; Naoki Tsukamura; Yoshinobu Uchimura; Toshifumi Shigematsu; Hironori Yamaski; and Toshio Yamaguchi It is certified that error appears in the above-indentified patent and that said Letters Patent is hereby corrected as shown below:

Column 24, line 50, (Claim 15, line 5,) change "bow" to --bowl --.

Column 28, line 30, (Claim 34, line 26,) insert after "and" (first Occurence) --display means associated with said toilet device for controlling said sliding --.

Signed and Sealed this

Thirteenth Day of July, 1993

Attest:

MICHAEL K. KIRK

*Attesting Officer*  Acting Commissioner of Patents and Trademarks